(12) United States Patent
Hamada

(10) Patent No.: US 8,236,006 B2
(45) Date of Patent: Aug. 7, 2012

(54) ONE STEP ENTRY PEDICULAR PREPARATION DEVICE AND DISC ACCESS SYSTEM

(75) Inventor: James S. Hamada, Torrance, CA (US)

(73) Assignee: Life Spine, Inc., Hoffman Estates, IL (US)

( * ) Notice: Subject to any disclaimer, the term of this patent is extended or adjusted under 35 U.S.C. 154(b) by 497 days.

(21) Appl. No.: 12/321,311

(22) Filed: Jan. 15, 2009

(65) Prior Publication Data
US 2009/0187194 A1    Jul. 23, 2009

Related U.S. Application Data

(63) Continuation-in-part of application No. 12/009,496, filed on Jan. 17, 2008, now Pat. No. 8,075,579.

(51) Int. Cl.
*A61B 17/58* (2006.01)
(52) U.S. Cl. ...................................... 606/104
(58) Field of Classification Search .......... 600/426, 600/427, 429; 606/279, 292, 266, 312, 318, 606/916, 79, 60, 61, 63
See application file for complete search history.

(56) References Cited

U.S. PATENT DOCUMENTS

| | | | |
|---|---|---|---|
| 5,171,279 A * | 12/1992 | Mathews | 128/898 |
| 6,175,758 B1 | 1/2001 | Kambin | |
| 7,494,489 B2 | 2/2009 | Roh | |
| 2005/0251139 A1* | 11/2005 | Roh | 606/61 |
| 2006/0079903 A1 | 4/2006 | Wong | |
| 2007/0016219 A1 | 1/2007 | Levine | |
| 2008/0086140 A1 | 4/2008 | Wolf | |
| 2009/0254131 A1 | 10/2009 | Roh | |

FOREIGN PATENT DOCUMENTS
WO    WO 2009/091616 A3    7/2009

OTHER PUBLICATIONS

Written Opinion of the International Searching Authority for PCT/US2009/000393, dated Aug. 27, 2009, 6 pages.
US Office Action for U.S. Appl. No. 12/009,496, mailing date Apr. 20, 2011, 16 pages.

* cited by examiner

*Primary Examiner* — Eduardo C Robert
*Assistant Examiner* — Ann Schillinger
(74) *Attorney, Agent, or Firm* — Foley & Lardner LLP

(57) ABSTRACT

A one step entry pedicular preparation device works well with Minimal Invasive Spine Surgery (MISS) to facilitating such approach. A related intervertebral disc access system and pedicle screw compatible with the systems is also illustrated. The systems include a manipulator having a bar handle and main body with main barrel bore a pedicle dart having a proximal tip end and a second distal open end selectably attachable to the manipulator using a variety of interconnect configurations, both of which work in conjunction with a guide pin. The pedicle darts can be made of any material, disposable or re-usable and can be utilized for a variety of purposes, including bone structure formation for faster conventional pedicle screw insertion with precision and vertebra fixation.

18 Claims, 23 Drawing Sheets

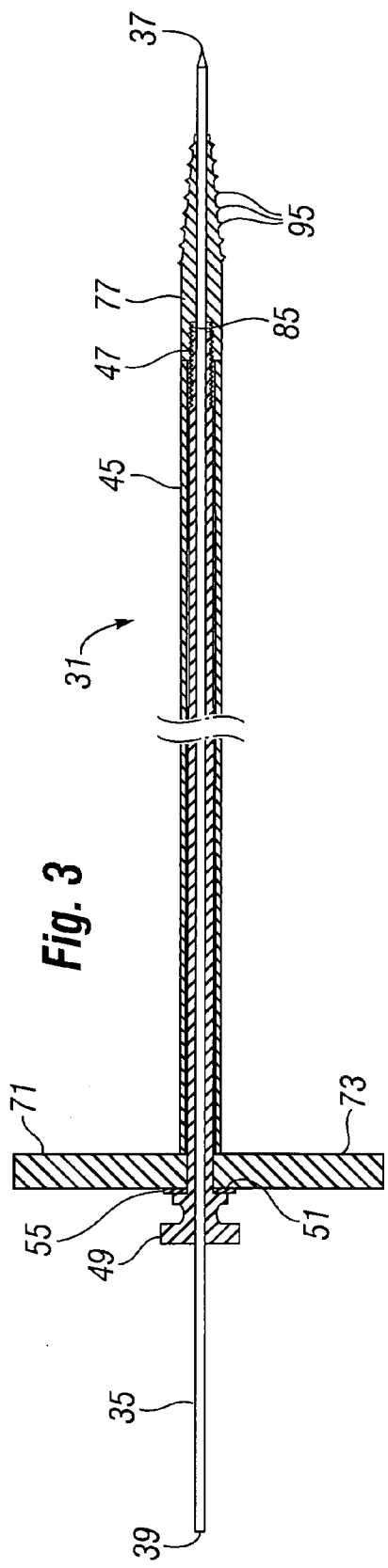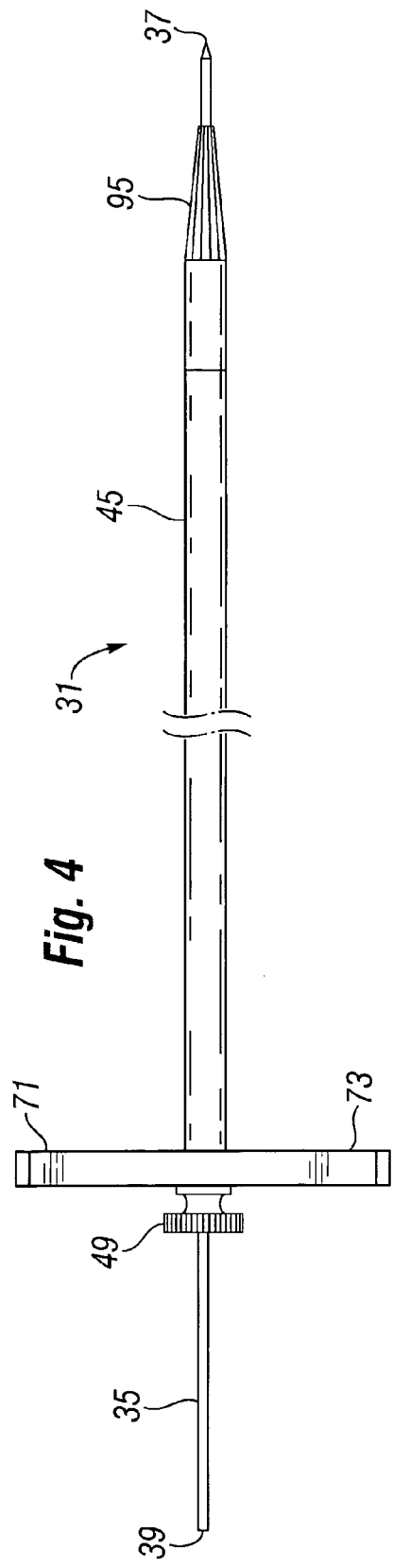

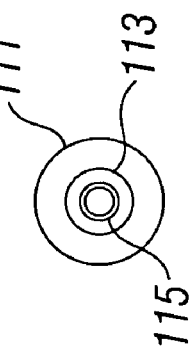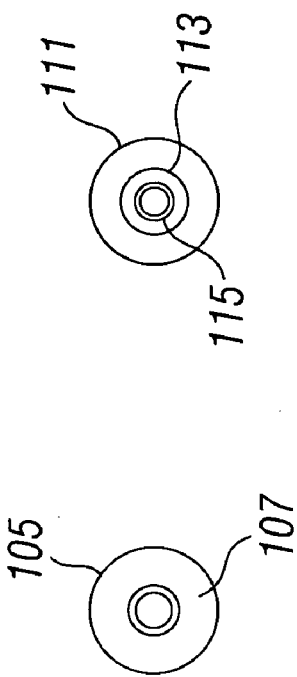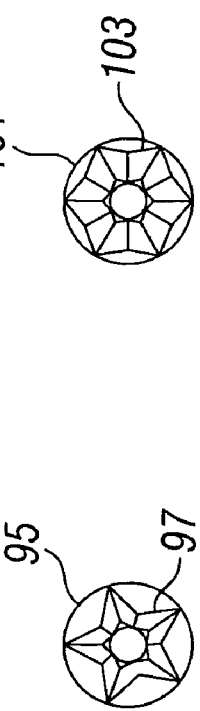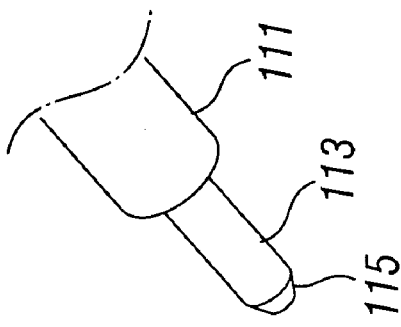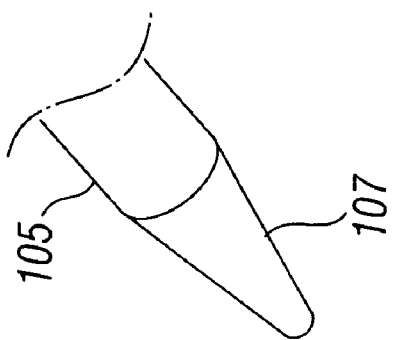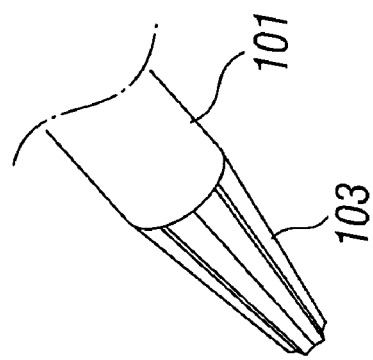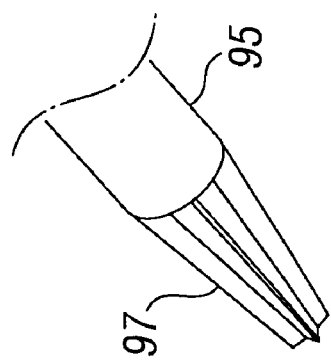

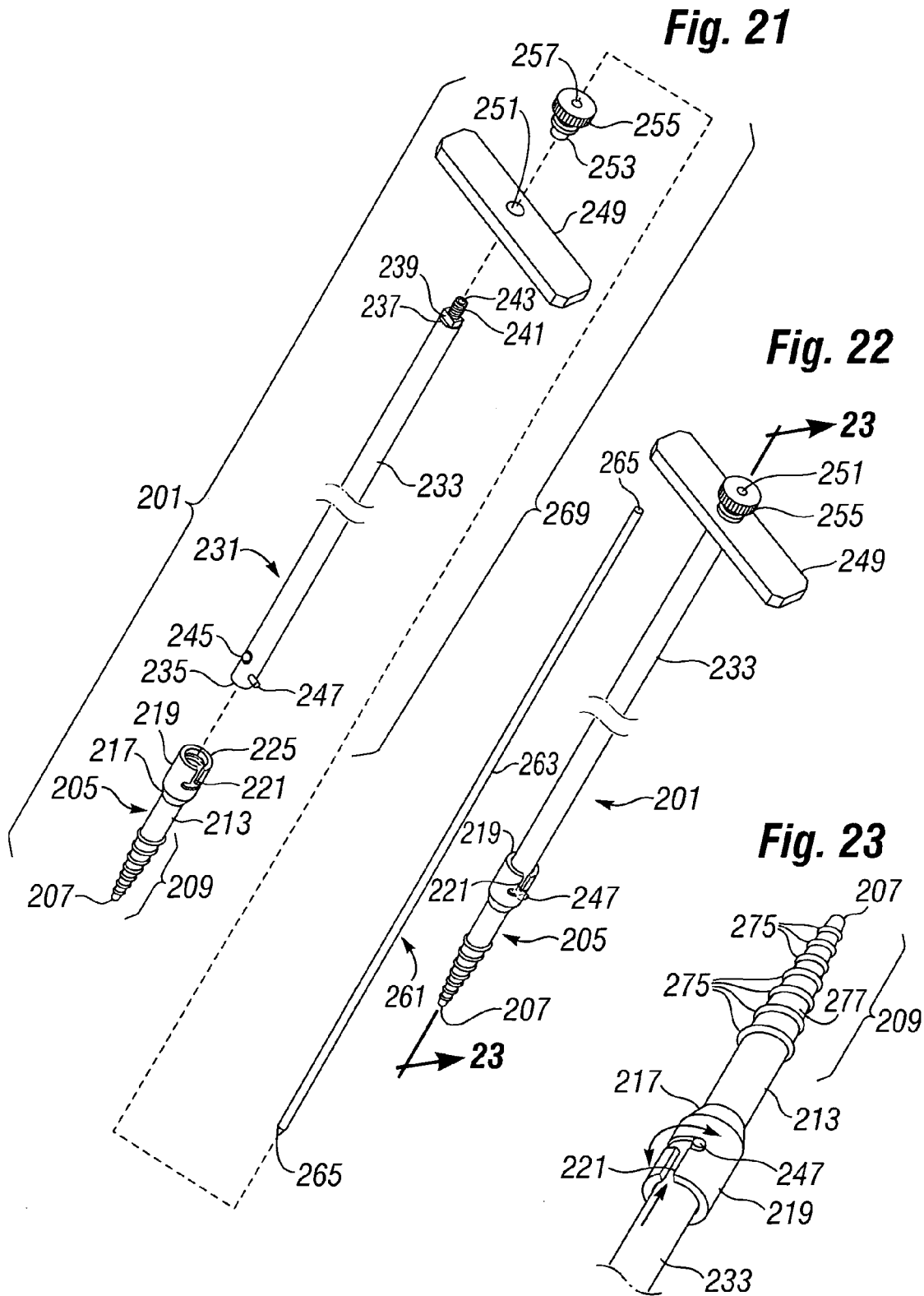

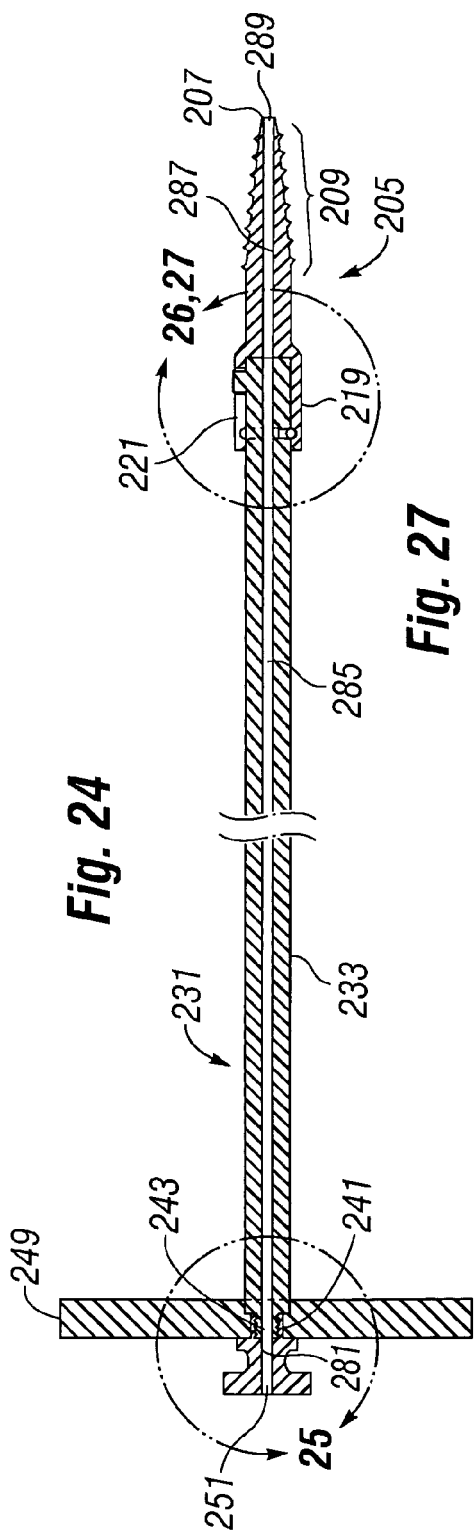
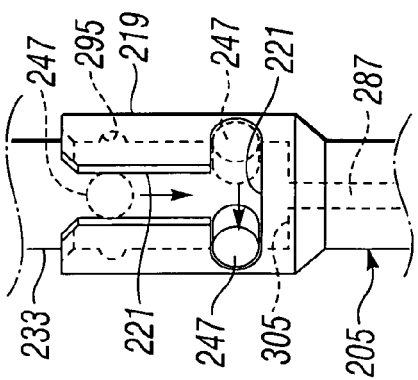
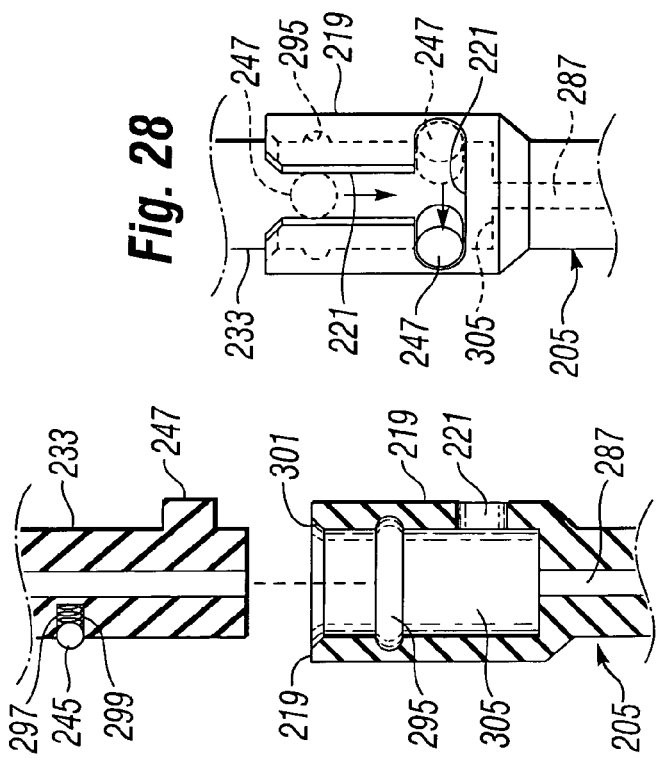
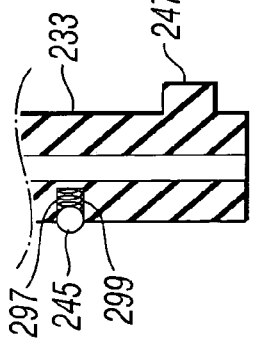
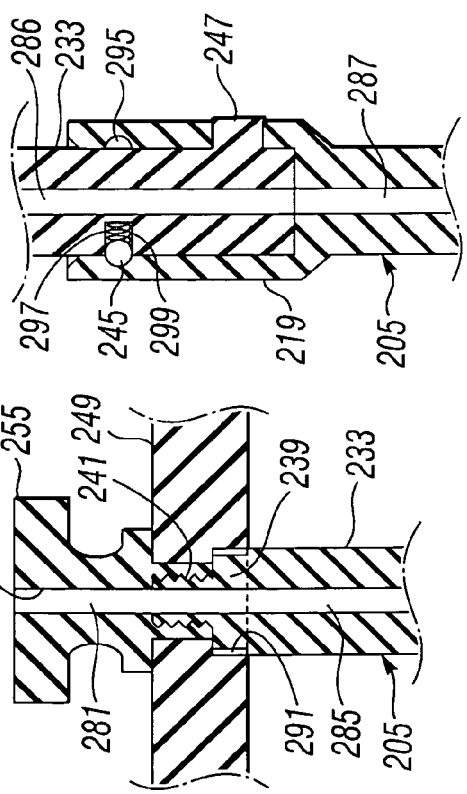

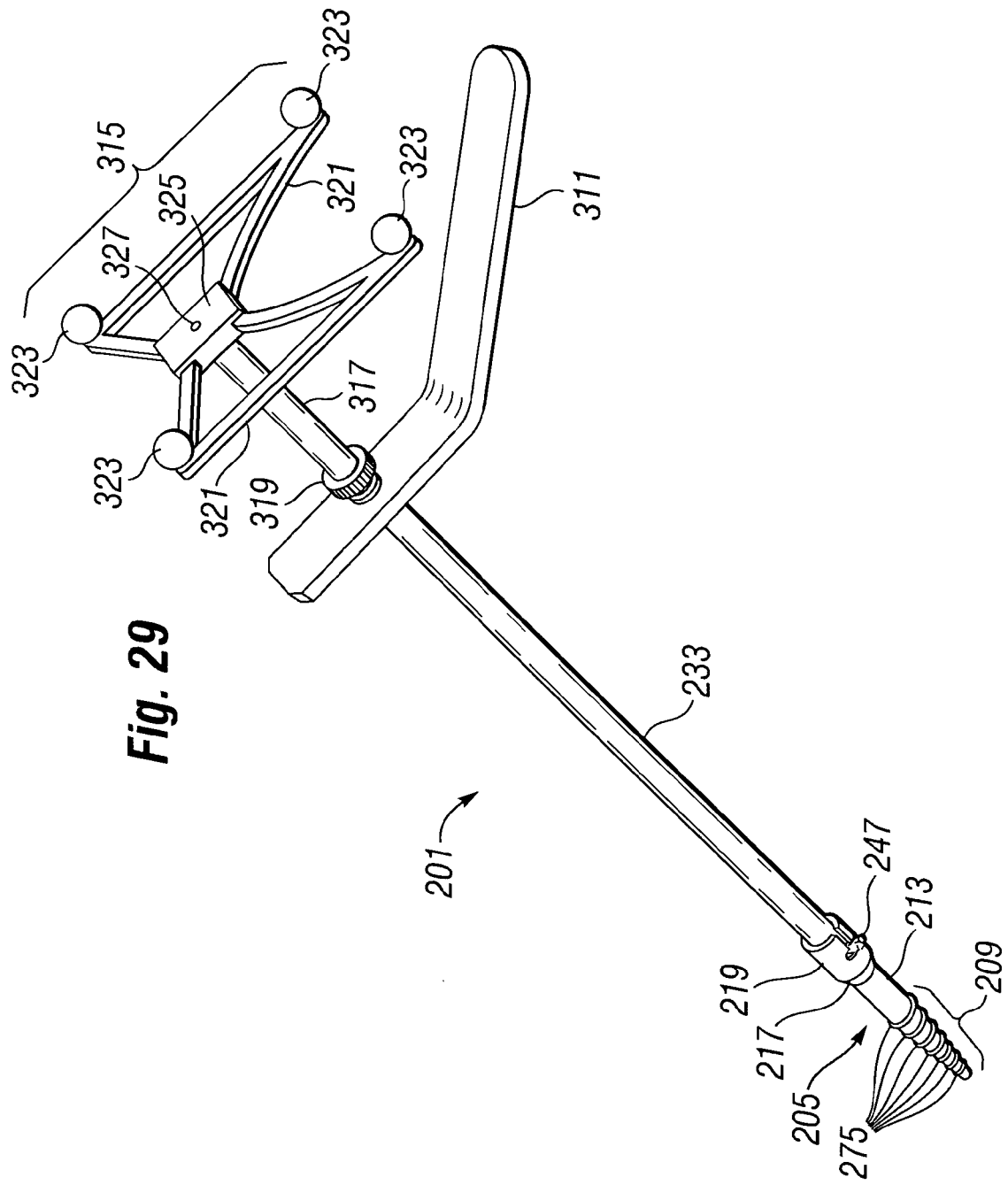

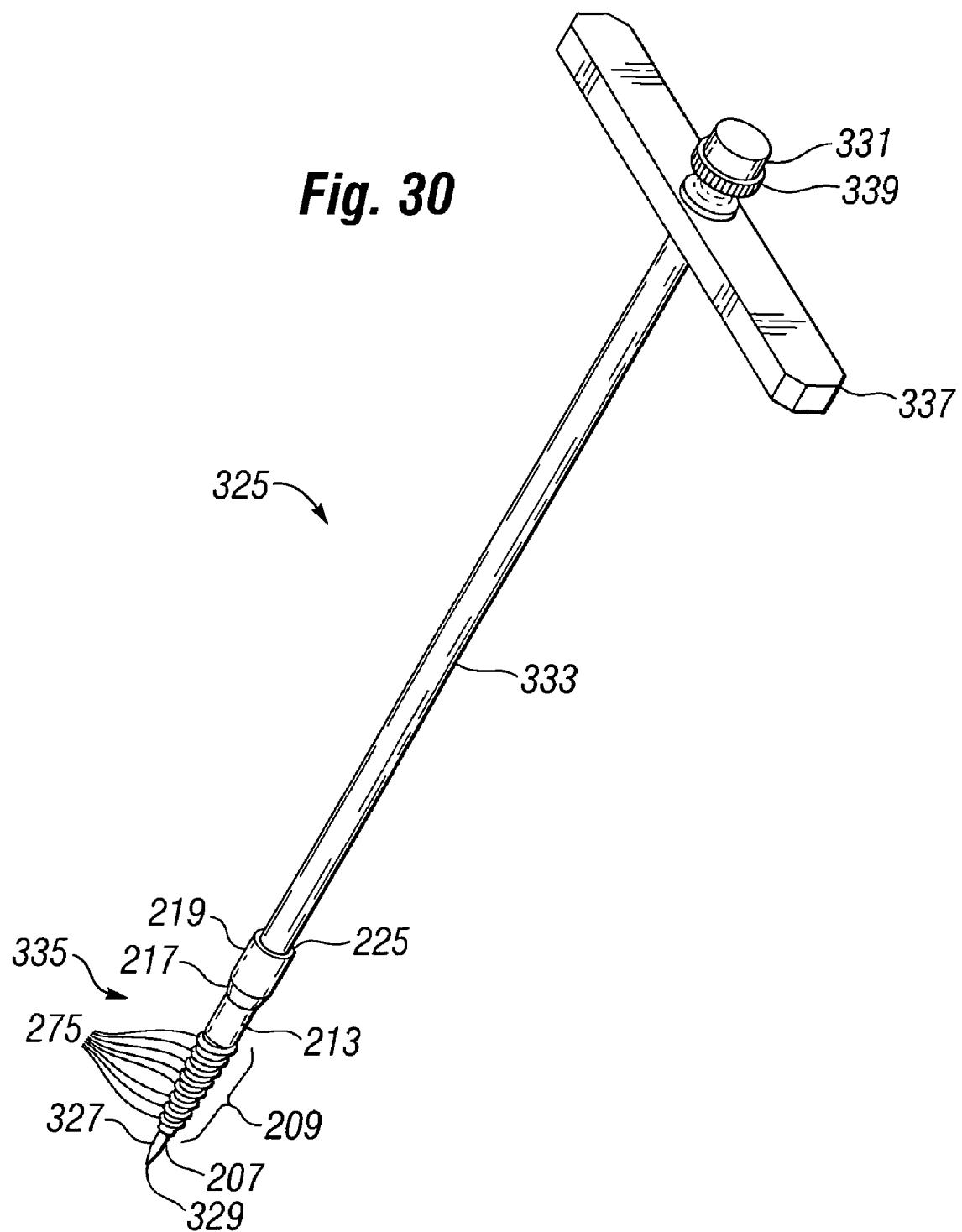

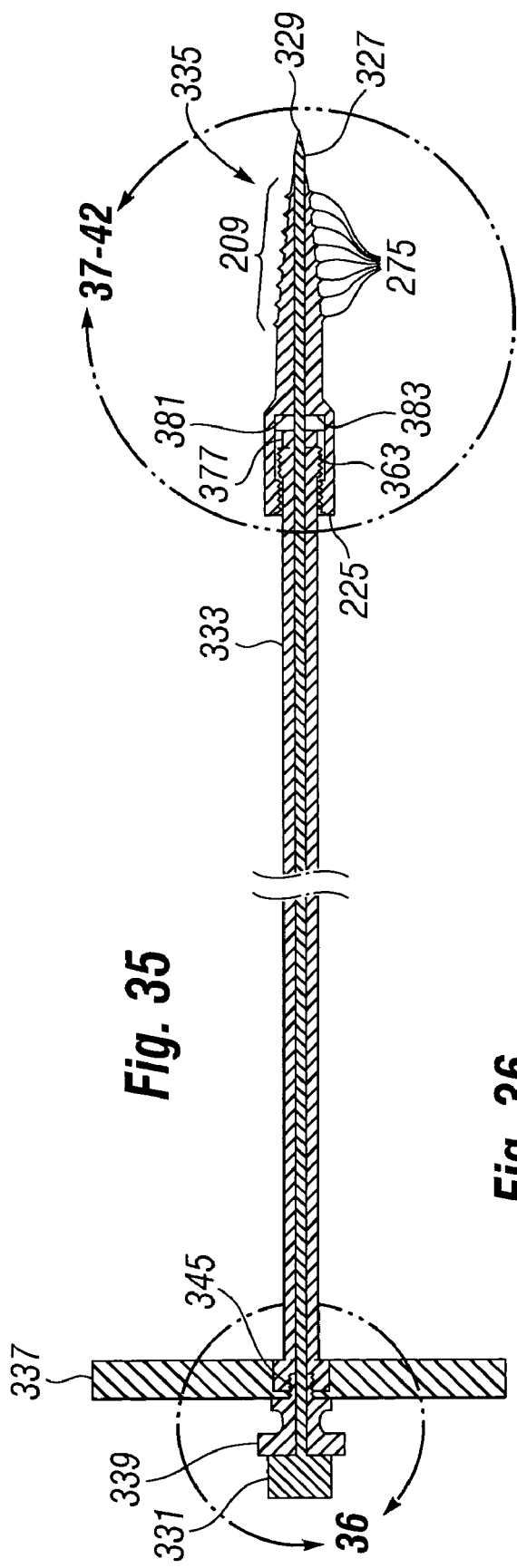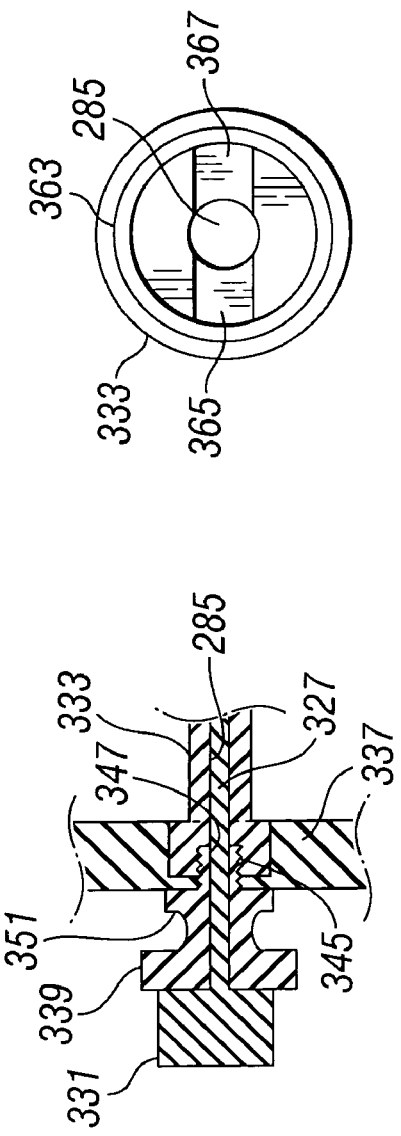
Fig. 34
Fig. 35
Fig. 36

ONE STEP ENTRY PEDICULAR PREPARATION DEVICE AND DISC ACCESS SYSTEM

This is a continuation-in-part of U.S. patent application Ser. No. 12/009,496 filed Jan. 17, 2008 now U.S. Pat. No. 8,075,579.

FIELD OF THE INVENTION

The present invention relates to improvements in the field of spine surgery and more particular to a system for the ability to perform spine surgery through a small opening, the location, placement, and insertion of temporary pedicular implants called PediDart™ pedicle darts which are applicable to both MIS and open surgical technique and which allows for more exact and rapid placement with correct angular insertion of fixation members into the spinal pedicle, which will facilitate one of the most difficult phases of spine surgery. The result is increased safety of placement and insertion of the pedicle screws, avoiding potential devastating complications to the adjacent neurovascular structures as well as less time spent on the operating table. The same basic design of the PediDart™ pedicle dart system with minor but important modifications can then be applied to percutaneously access the intervertebral discs for the purpose of biopsy or implantation of stabilizing or bioactive materials.

BACKGROUND OF THE INVENTION

Surgical procedures in general and spine surgical procedures in particular have progressively evolved to a minimally invasive approach over the past two decades. The advantages for the patient have been well documented with less pain, blood loss and tissue damage all contributing to a faster recovery and improved function with fewer complications. However, the smaller exposure of the surgical field has presented a challenge to the surgeon to accomplish the same goals of a successful open procedure with a technique thatless direct visualization of the operative site. To perform surgery through a smaller opening with maximum safety to the patient, newer tools and inventions have become necessary. The PediDart™ pedicle dart system contributes to the growing but still deficient list of tools required to perform safe, minimally invasive spine surgery.

Spinal fusion with internal fixation instrumentation using pedicle screws have become the "gold standard" for posterior thoracic and lumbosacral fusion using internal fixation. For optimal results and safety it is required to accurately place bone screws (pedicle screws) from the outer surface or cortex of the pedicular segment of a vertebrae and advance down the cancellous core of the pedicle to engage the threads of the screw into the body of the vertebrae. Two or more adjacent vertebra are then connected by placement of rods transfixed to the pedicle screws by a locking cap or nut, or by crimping.

To the accomplished spine surgeon such insertion of a pedicle screw is most commonly accomplished by first perforating the entry into the pedicle located at the junction of the transverse process and superior facet with a pointed metallic probe, and then following the path of least resistance through the cancellous core of the pedicle and then into the vertebral body. Proper location of the metallic probe is confirmed with x-ray or other navigational method. The path created by the probe is then tapped or threaded to prepare for placement of the pedicle screw of the proper length and dimension.

Improper or inaccurate placement of the pedicle screw can result in catastrophic injury to neurological, vascular or bowel structures or inadequate purchase of the screw to the bony vertebra resulting in unstable fixation and failure of fusion. Malplacement of pedicle screws have been reported to occur between 6-12% when evaluated by plain x-rays and up to 35% when examined with the more accurate axial computerized tomography techniques. Serious complications from malpositioned pedicle screws are approximately 2% due to the anatomic "safety margin" leaving adequate space between the vital neurologic structures and the bony spinal canal to accommodate for the error.

Nevertheless, a more exact and precise way to accurately insert a pedicle screw into the thoracic lumbosacral spine is not only desirable but necessary. Improved techniques and instruments are especially needed when "percutaneous" methods of spinal fixation are utilized such as with the "pathfinder" system (Abbot Spine), Expedium (Depuy) or Sextant (Medtronics) to name a few systems. The method of pedicle screw placement with the percutaneous systems are to first localize the entry point with fluoroscopic imaging passing a Jamshidi needle/probe through a small skin incision, docking into the pedicle entry point and then driving the Jamshidi probe through the pedicle into the vertebral body. This is followed by the insertion of a guide pin over which a cannulated tap is applied followed by pedicle screw placement. Infrared navigational methods can also be used to guide placement of the pedicle screw.

There are several drawbacks and limitations with the current technique of pedicle screw insertion. This technique has also been referred to as the "feel" technique.

(1) Entry point location by surface anatomical features are inaccurate due to bony anomalies. Variations of development, bony bumps and spurs develop differently with time.

(2) Incorrect entry points can lead to trajectory error which can result in perforation of the pedicular wall. Medial perforation will jeopardize neural structures or epidermal vessels. Lateral perforation will result in lack of stability due to failure of the screw engaging the vertebral body.

(3) The cancellous core of the pedicle may be too small (type B pedicle) or non-existent (type C pedicle) or lack continuity (type D pedicle) to allow accurate passage through the center of the pedicle to engage the vertebral body.

(4) The use of the hand-held metallic probe is physically arduous leading to surgeon fatigue.

(5) Additional steps of sequential tapping require time prior to final screw placement.

Further, the percutaneous technique has the following drawbacks.

(1) the Jamshidi probe is too flimsy and often too short, making it difficult to properly dock onto the entry point.

(2) The Jamshidi probe is too flimsy to navigate down a hard pedicle without deviating from the center of the pedicle.

(3) At times even after the vertebral body is reached, the guide wire is difficult to advance through hard bone.

(4) The additional steps of sequential tapping is required before placement of the pedicular screw.

Inaccurate placement of the pedicle screw may result in damage to the vertebrae such that screw insertion may not be possible, or if it can be achieved it may require additional surgical procedures for correction to provide the necessary holding strength.

Other conventional techniques for insertion of the pedicle screw may involve extensive paraspinous muscle dissection, impairment of surrounding tissue and other compromising tissue removal commonly necessary to properly insert a pedicle screw. This most often results in significant blood loss during this exposure phase of the operation, which is only one part of a multiple step operative procedure. Any problems at any stage of an operation can risk the patient's safety and surgical outcome.

The surgical practitioner is faced with the choice between high exposure and a good view but increased tissue damage, versus a more limited exposure with a much poorer view and a heightened risk of a wrong insertion of the pedicle screw, but with potentially better outcome.

What is needed is a system which will enable correct placement of a pedicle device, accurately and consistently and which will not require extensive paraspinous muscle dissection for proper placement. The needed device will ideally enable a gradual graded introduction into the pedicle and give an earlier indication of problems so that any error can be quickly corrected at a time before the introduction goes any further.

Currently available surgical retractor systems fail to fulfill all of the above requirements. Consequently there is a severe need for complementary tools and inventions to meet the requirements of precise, safe and timely spine fusion surgery.

SUMMARY OF THE INVENTION

The system and method of the invention, illustrates a variety of structures and techniques to enable a staged location and entry into the pedicle for providing insertive, progressively larger threaded fixation and superior surgical control a distance from the spine. The PediDart™ pedicle dart system offers a one step preparation for pedicle screw insertion in the safest and most accurate way possible with current imaging technology which may include x-ray or infrared, or RF navigational guidance. This allows for faster complex spine surgery procedures, decreased cost, decreased anesthesia time and complications such as surgery time dependent post operative infections. The device and method can be utilized manually or power driven and can be used open, minimal open or percutaneous surgical approaches.

The advantages of the PediDart™ pedicle dart system includes:

(1) The larger than usual guide pin (of about 2 millimeters in diameter) allowing for a sharper and more stable trocar point to precisely dock and hold to the entry point without slippage.
(2) The larger guide pin resists bending and consequently binding which is a major drawback to current guide pin systems.
(3) The limited exposure length of the guide pin not only resists bending, but minimizes excessive penetration in the spine and beyond which can result in vascular or bowel injury.
(4) The tip end of the PediDart™ pedicle dart system begins with a cutting thread to quickly capture the cancellous bone in the case of the bony pedicle.
(5) The PediDart™ pedicle dart systems fluted shaped advances smoothly down the inner pedicle and gradually expands the cancellous inner bone so that sequential tapping is not necessary.
(6) The fluted shape can also safely expand immature pedicular bone such as with adolescent idiopathic scoliosis surgery allowing placement of the largest pedicle screw for the best stability.
(7) The non-cutting threads at the larger end of the flute compresses and strengthens the cancellous pedicular bone to give better purchase to the pedicle screw.
(8) The smaller diameter of the entry end of the PediDart™ pedicle dart system preserves the bone in the vertebral body for best pedicle screw purchase especially important for the osteopathic spine.

(9) The cone shaped channel created by the fluted PediDart™ pedicle dart system allows maximum contact to the entire length of the pedicle screw.
(10) The cone shaped channel created by the PediDart™ pedicle dart system allows for accurate advancement of the pedicle screw.
(11) The smooth part of the shank gives greater length to the PediDart™ pedicle dart system when used as a temporary implant to compress or distract a motion segment such as for the placement of an intervertebral or disc space implant.
(12) The sloped buttress at the tail end of the PediDart™ pedicle dart system keeps the system from excessive penetration.
(13) The sloped buttress at the tail end provides for a "flared" entry point for the pedicle screw.
(14) The inner slot and lock mechanism provides the most powerful way to rotate the PediDart™ pedicle dart system into and out of the spine.
(15) The "hockey stick" shaped external slot provides an additional way to remove the PediDart™ pedicle dart system when it is deeply inserted in a large patient, and particularly where some other object or tissues blocks rearward motion of the pedicle dart.
(16) The tapered inner hollow structure facilitates proper engagement between the pedicle dart and the manipulator/insertion tool.
(17) The inner spring of the PediDart™ pedicle dart system mates to the circular slot of the insertion tool/manipulator capturing the pedicle dart but yet still allows for disengagement.
(18) The handle of the insertion tool/manipulator is designed for the best tactile feel and control for the surgical practitioner.
(19) The modular end of the insertion tool/manipulator can adapt for navigational points, impacting tool or power attachment.
(20) The length of the insertion tool/manipulator keeps the surgeon's hands away from the x-ray beam.
(21) The PediDart™ pedicle dart system can serve as a temporary implant, a permanent implant or a structure for a stand alone screw and rod system. It can also be adapted for intervertebral disc access ("Disc PediDart™").

A first embodiment of the pedicle dart system is simple and has a small number of components. These components include a guide pin, a pedicle dart fastener (preferably having some control structure for easy manual rotation) having a central opening to accommodate the guide pin, an indexed sleeve (preferably with handle) having a central opening to accommodate the threaded pedicle dart fastener to hold the dart to the sleeve. The threaded pedicle dart fastener should have a manual control surface which facilitates it axial rotation with respect to the indexed sleeve. The indexed sleeve preferably has a handle to enable rotational turning of the pedicle dart into the pedicle for ease and control.

The first embodiment of the pedicle dart system enables use of the threaded pedicle dart fastener to both engage and disengage from an implaced pedicle dart. The indexed sleeve can impart rotational force of the sleeve directly into the pedicle dart due to the indexed connection between the pedicle dart and indexed sleeve. The threaded pedicle dart fastener is used to engaged and pull the pedicle dart to an indexed position with respect to the indexed sleeve.

The preferred method of indexing for the first embodiment involves a pair of oppositely located fingers at the end of the indexed sleeve which are narrower than indexed slots located rearward of each of the pedicle darts. By making the fingers of the indexed sleeve narrower than the indexed slots rearward of each of the pedicle darts, the registry of the fingers of the indexed sleeve into the pedicle dart slots will occur much more rapidly. This enables easy location and re-attachment of the pedicle screw no matter whether the pedicle dart is attached away from the patient by hand or whether an implaced pedicle dart is re-attached for engagement with the pedicle dart system to remove it.

Further, the first embodiment of pedicle dart system also contemplates the use of the darts as starter devices to facilitate the placement of larger and higher profile conventional pedicle screws where necessary. In this limited view of the system, it can be viewed as a pedicle screw bore starter while eliminating the need to perform undue paraspinous muscle disturbance.

Moreover, as designed, one of the important aspects of the pedicle dart system involves the location of smaller fixation structures (pedicle darts) which have a lesser upward projection from the lumbar vertebra during the operation. This enables a major advance over the conventional art in which the need to place pedicle screw fixation devices before the surgical procedure often get in the way of (a) the ability to manipulate manual instrumentation to accomplish the procedure, (b) other structures used with the procedure, and (c) general visual obstruction of the surgical area.

The pedicle darts can be made in a variety of sizes, all of which can exhibit a much lower profile adjacent the surgical area. Conventional pedicle screws project high on the patient, perhaps to overcome the difficulty which would accompany conventional methods of accessing the conventional pedicle screws. The pedicle dart system provides instrumentation to reach in and re-engage otherwise hidden pedicle fixation devices. The pedicle dart system of the invention can also enable located re-attachment of larger pedicle darts or pedicle dart extensions to form the fixation needed. Conventional pedicle screws have a proud, high profile proximal connecting end which can impair access to placing intervertebral implants such as with a TLIF procedure. The pedicle dart system enables a level of flexibility not seen in conjunction with other fixation devices.

Further, it is not required that the darts must be able to be inserted using a thread. They can be inserted by pushing or turning, such as acting to bore into the bone using a non threaded action. Such shapes may be advantageous in removing bone in a way that will not bind or tend to put significant lateral pressure on bone tissue in the pedicle.

The use of the pedicle dart system provides a high number of significant advantages over the use of conventional pedicle screws.

1. The pedicle dart system enables the use of percutaneous technique, with the result that there is much less blood loss.
2. The pedicle dart system is completely compatible with the use of bi-planer fluoroscopy or navigational method, especially with the elongated components, allowing the insertion of the pedicle dart in a much can be precise manner.
3. The pedicle dart system facilitates placement of a temporary pedicle dart which decreases blood loss from the hole or bore in which the pedicle dart is implaced.
4. The pedicle dart system enables the use of a low-profile pedicle dart that does not interfere with retraction blades, thus allowing for greater visibility of the surgical field.
5. The pedicle dart system enables percutaneous localization of the pedicle and insertion of the pedicle dart as a marker decreases the necessity of wide muscle stripping and therefore patient damage.
6. The pedicle dart system enables the use of a technique that allows for the preservation of the vascularity and the innervation to the longissimus muscle, which always had to previously be sacrificed using the traditional (non-pedicle dart technique). The avoidance of destruction to the longissimus muscle allows for a healthier paraspinous muscle and decreases the incidence of chronic pain associated with de-vascularized fibrotic paraspinous tissue.
7. Traditional placement of the conventional pedicle screw has high incidence of association with breach of the pedicular wall, which can lead to serious complications. The precision placement of the trans-pedicular path using the pedicle dart technique will minimize such complications.
8. Most important, there is a significant surgical time-saving component, as lengthy muscle dissection and direct exposure will no longer be required.
9. The shortened surgical time will mean less surgical time, providing significant cost savings for the entire health-care system.

A second embodiment of the pedicle dart system has a number of features where it is desired to have a quick-connect and quick-disconnect system. A "T" shaped slot on a pedicle screw which may include a number of structures transitioning to a higher diameter are illustrates. This second embodiment can be left as a marker and can be distracted or compressed more directly and more quickly than the first embodiment due to the quick engagement bi-directional engagement of the "T" shaped slot.

Both of embodiments of the dart herein may be expected to be disposed of after a single operation. Otherwise the darts might become dull with use, including the forward cutting edge and the threads. A number of transition surfaces assist the practitioner in making a stop and insuring that the pedicle dart can go forward only so much as is necessary. The "T" slot of the second embodiment will also assist the practitioner in ascertaining depth, and in watching the number of full rotations. The "T" slot provides for instant rotational engagement and actuation in either the clockwise or counter clockwise position. Further, the quick connect and disconnect enables the surgical practitioner to start and advance or remove several pedicle darts serially, without having to engage and disengage a central member after engagement by finger projections.

In the second and further embodiments, the pedicle dart may be about five centimeters long and have a number of cylindrical and conical surfaces which increase in diameter from the distal tip to the proximal engagement end. The five centimeter length may include about two and a half centimeters of tapered threaded surfaces, about one and a half to two centimeters of a cylindrical portion, and then an optional conical transition portion which may have an axial length of about two millimeters to about four millimeters in length. An engagement portion may have a length of about one centimeter.

The proximal tip may be a diameter of about two millimeters. The cutting tip may have a thickness of from about one tenth of a millimeter to about five tenths of a millimeter. The diameter of the distal portion of the tapered or gentle conical threaded portion may be about one half of a centimeter. The thread pitch may be from about four to six per centimeter of axial length of the pedicle dart. The threads are preferably of low height, typically from about two tenths to about six tenths of a millimeter and a width from about two tenths to about six tenth of a millimeter and having a shape which rises evenly about their radially spiral extent from the tapered frusto-conical shape. Given that bone is soft, the threads are used more as a guide to help the practitioner set the rate at which the darts are inserted, rather than used to engage and advance the dart. Further, the low height threads can be used to advantage for a number of purposes. The shallow threads serve as a visual indication of insertion and extraction progress with the amount the length of the threads serving as a progress gauge. The extent that positive urging force accompanies a rotational force, the low height threads, coupled with a visual insertion, helps the surgical practitioner have a better and more cautious approach on insertion. The amount of pressure needed for insertion will be high for rapid insertion and low for extremely slow insertion, but the ability to view the threads upon insertion gives the surgical practitioner a feedback which is matched to a rate of insertion. The rate is visually ascertainable by seeing whether the insertion of the threaded portion enters in a way which either tracks the turning of its threads, is ahead of the turning of its threads or lags the turning of its threads.

Further, when the pedicle dart of the invention is used to help remove material especially in contemplation of insertion of a regular pedicle screw, the turning of the pedicle dart without advancing the pedicle dart enables the low height threads to act as a gentle auger for removing bone from the formed bore and for scrapingly smoothing the formed bore. Especially in pediatric patients, the ability to perform a gentle auguring of the pedicle bore prior especially where the pedicle dart is used to lead the way for insertion of a pedicle screw, can be advantageously much more safely performed.

The shallow threads avoid cutting the bone too deeply which could weaken the all of the pedicle. The dimensions for the second embodiment may preferably protrude above the operative field up to about one centimeter when the pedicle dart is fully inserted. Further, a larger, longer pedicle dart having a series of stepped or conical tapered transitions can enable a longer guide pin, and possibly a lager guide pin for greater stability, particularly where the intermediate member for threaded engagement, which lies between the guide pin and the outer housing, is eliminated.

Further, the second embodiment is particularly amenable to have a use as a one step entry pedicular preparation device. With one device setup, the surgical practitioner can, preferably using fluoroscopy, locate an entry point, insert the guide pin, enter with the preparation device and do so slowly and deliberately, but cautiously to reduce mis-alignment. This one step entry pedicular preparation device has a unique design with a sturdy, stable guide pin which protrudes approximately one centimeter from the end of the second embodiment of the pedicle dart in order to allow for a more accurate starting point on the uneven external bony surface of the pedicle. The somewhat stiffer and length of the exposed guide pin is designed to allow better steering into the center of the pedicle and minimize bending as the pedicle dart is turned and advanced into the bone.

Unique features of the pedicle dart system provide for a one step entry and preparation of the pedicle which precedes insertion of a properly sized pedicle screw of any design. The tip of the guide pin and the tip of the pedicle dart is sharpened to penetrate the external surface of the bone, but its round shape keeps it tracking along the center of the pedicle entry point and through the pedicle without penetrating the surrounding wall. The gentle tapering of the pedicle darts allows for concentric expansion of the bony pedicle to prepare for acceptance of the largest pedicle screw to be inserted. The gentle taper also ensures maximum purchase of the pedicle screw threads into the bone. The largest diameter formed by the entry of the distal, tailed end of the pedicle dart is sufficient to permit subsequent ease of insertion of the pedicle screw.

The low height, spaced apart threads can allow rapid, but easily visually controllable advancement. The flat conic surface between adjacent threads is designed to expand and compress the cancellous bone instead of cutting a track which my perforate the wall. This gives control, an internal "pedicle trapping" action and makes the one step entry pedicular preparation operation smooth, secure and reduces error.

The one step entry pedicular preparation device and system of the invention facilitates a percutaneous surgical method:

(1) Localize the entry point of the selected pedicle using a c-arm. Adjust the c-arm to center the spinous process in the vertebra on the AP projection. Tilt the c-arm to best define the superior and inferior end plate with maximum dimension to the pedicles.

(2) Mark a point on the skin from one to three millimeters lateral to the nine o'clock position for the left pedicle and lateral to the three o'clock position for the right pedicle. Lateralization depends on the vertebra, with greater lateralization for the more caudal lumbar vertebra.

(3) make a one centimeter stab wound at the marked position.

(4) Insert the PediDart™ pedicle dart system with the guide pin retracted into the pedicle dart and advance the insertion tool/manipulator to the pedicular entry point.

(5) Stabilize the PediDart™ pedicle dart system on the entry point by impacting the guide pin into the pedicle.

(6) Confirm proper placement and trajectory with the c-arm and make corrections as necessary.

(7) Impact the PediDart™ pedicle dart system to engage the pedicle dart threads into the pedicle and then rotate the insertion tool/manipulator advancing the pedicle dart into the pedicle and vertebral body.

(8) Either leave the PediDart™ pedicle dart as a temporary implant or insert the pedicle screw specific guide pin and remove the PediDart™ pedicle dart.

(9) Insert the pedicle screw over the guide pin into the PediDart™ pedicle dart prepared channel to the appropriate length Surgical technique for an open surgery is the same as the nine step method described above but begins at step (4) with the first three steps being un-necessary.

In terms of size and materials, the PediDart™ pedicle dart system can be manufactured with other sizes and shapes depending upon the intended application. For example, a smaller size may be necessary for the upper thoracic spine in a younger patient. Other applications other than pedicle screw preparation are also possible such as percutaneous disc space entry for biopsy or insertion of an implant or biologically active material. The PediDart™ pedicle dart system can also be used for lateral an anterior approaches to the spine using a blunt tipped guide pin for advancement to the spine. The PediDart™ pedicle dart system is also intended as a single use disposable device for maximum safety and optimal performance, especially where the pedicle dart is made of hard plastic or composite material. Other materials can be metals, or other materials yet to be developed.

BRIEF DESCRIPTION OF THE DRAWINGS

The invention, its configuration, construction, and operation will be best further described in the following detailed description, taken in conjunction with the accompanying drawings in which:

FIG. 3 is a sectional assembled view illustrating the interfitted components of the basic pedicle dart system;

FIG. 4 is a plan assembled view illustrating the interfitted components of the basic pedicle dart system with a further embodiment of a pedicle dart having conically tapering exterior ribs;

FIG. 5 is an expanded perspective view of the pedicle dart seen in FIG. 4 illustrating the taper and ribs;

FIG. 6 is an end view of the pedicle dart of FIGS. 4 and 5 illustrating the geometric shape as having deep ribs, which are five in number;

FIG. 7 is an expanded perspective view of a further embodiment of the pedicle dart as having a taper, but with more shallowly formed and more numerous ribs;

FIG. 8 is an end view of the pedicle dart of FIG. 7 illustrating the geometric shape as having shallow ribs, which are six in number;

FIG. 9 is an expanded perspective view of a further embodiment of the pedicle dart as having a conical taper;

FIG. 10 is an end view of the pedicle dart of FIG. 9 illustrating the geometric conical shape;

FIG. 11 is an expanded perspective view of a further embodiment of a pedicle dart formed as a probe having a reduced diameter portion with an optional slight small end conical taper;

FIG. 12 is an end view of the pedicle dart of FIG. 11 illustrating the geometric stepped shape;

FIG. 21 is an exploded view of a second embodiment seen as a one step entry pedicular preparation device, which is shown along with a second embodiment of the pedicle dart;

FIG. 22 is an assembled view of the second embodiment seen in FIG. 21;

FIG. 23 is a closeup view of the second embodiment of the pedicle dart and its interaction with the end of the main barrel and illustrating the engagement projection and its operation within the "T" slot;

FIG. 24 is a sectional view of the one step entry pedicular preparation device seen in FIGS. 21-23;

FIG. 25 is a sectional view illustrating the detail taken along line 25-25 of FIG. 24 and illustrating the torque transmission block and its keyed entrapment within the t-handle support;

FIG. 26 illustrates an interaction of a detent ball and spring which can help provide a stable bi-positional force threshold for the pin and slot so that the pin will not disengage the slot unless the surgical practitioner affirmatively elects such action;

FIG. 27 is a sectional view as was seen in FIG. 26, but with the main body 233 shown detached from engagement with the pedicle dart to give a better view of the details of the inside of the upper sleeve of the pedicle dart;

FIG. 28 is a view looking directly into the "T" shaped slot to show the action and location of the pin and the positions it can occupy within the "T" shaped slot;

FIG. 29 illustrates a perspective view of the one step entry pedicular preparation device of the invention with a handle having an elongate and angularly raised member, emphasizing the modular and interchangeable nature of the second embodiment of the device, and shown with a navigation structure attached over the pin guide opening in order to enable a sensor to visually ascertain the position of the device;

FIG. 30 illustrates a further embodiment of the one step entry pedicular preparation device and system and also with a further embodiment of a guide pin and which has a further embodiment of a pedicle dart having a different operating mechanism than structures of the previous Figures;

FIG. 34 is a view looking into the pedicle dart along line 34-34 of FIG. 33;

FIG. 35 is an overall section view of the one step entry pedicular preparation device to orient a further series of sectional drawings;

FIG. 36 is a sectional view of the one step entry pedicular preparation device and system seen in FIGS. 30-35 and taken along line 36-36 of FIG. 35 showing further details of the interchangeable bar or other device utilizable to complete an overall one step entry pedicular preparation device and system;

FIG. 53 is a plan view of a pedicle screw which has an upper structure similar to that seen for pedicle darts in FIGS. 1-51, but which has a long even threaded profile for implantation into bone tissue, the upper structure being of variable configuration as to allow the attachment of rods, plates and other structure as needed.

DETAILED DESCRIPTION OF THE PREFERRED EMBODIMENT

Figure 1:
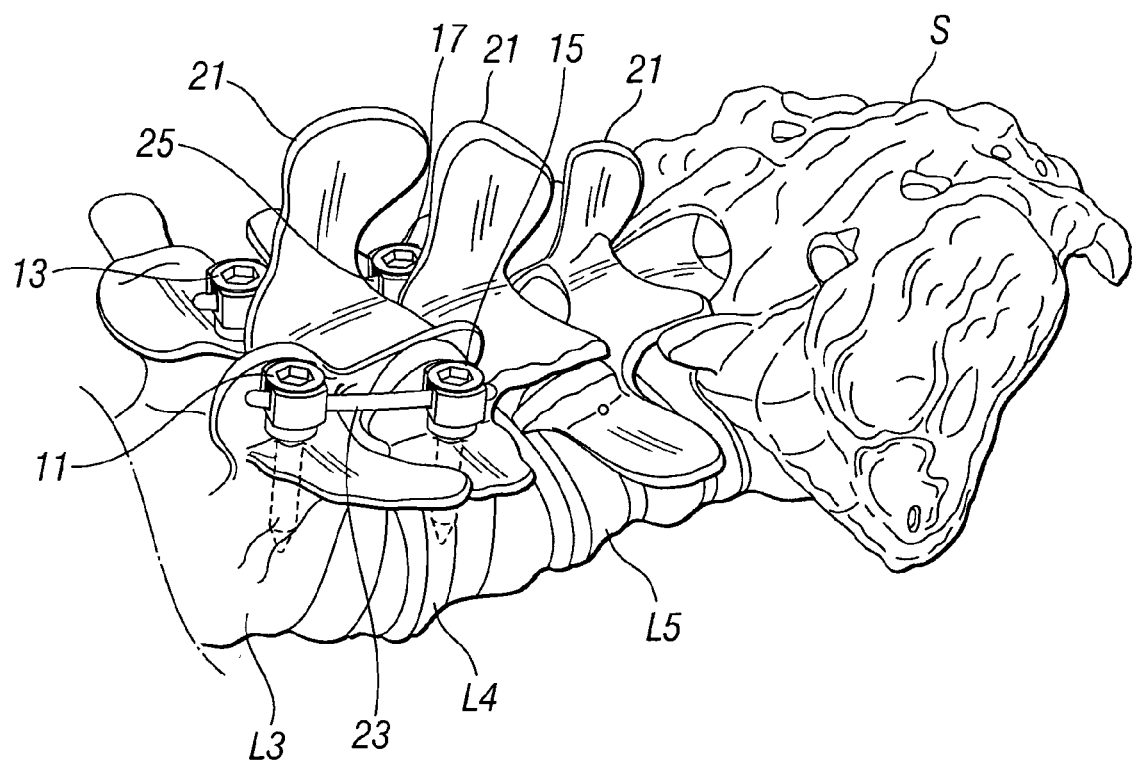
FIG. 1 is a perspective view of a prior art set of high profile conventional pedicle screws attached into the pedicles of two adjacent vertebrae and illustrating a fixation connector as an example of but one structure which can be used with pedicle screws.

A detailed description of the preferred embodiment will be best begun by examining a perspective view of the lower lumbar vertebrae L3, L4, L5 and sacrum S shown in perspective in FIG. 1. In operative procedures in which work is to be done between two adjacent vertebrae, those two vertebrae must be fixed and held apart so that the space between those vertebrae is maintained. Traditionally this has been done by using conventional pedicle screws 11, 13, 15 and 17 seen in FIG. 1. The conventional pedicle screws 11, 13, 15 and 17 engage significant bone mass by placement through the pedicle structure of each vertebra into which they are placed. In the three dimensional view of FIG. 1, the conventional pedicle screws 11, 13, 15 and 17 seem to have an open placement, during an actual surgical procedure on a patient, the pedicle screws 11, 13, 15 and 17 must be located through and despite significant layers of muscular tissue.

As previously discussed, dissection of the muscles surrounding the spiny process 21 of each of the vertebrae will damage the patient, permanently weaken the back and can delay or completely prohibit patient recovery. It is noted that the conventional pedicle screws 11, 13, 15 and 17 have a high profile, so high as to cause a similarly high engagement of an interconnect member 23 between conventional pedicle screws 11 and 15 and an interconnect member 25 between conventional pedicle screws 13 and 17. The use of two such interconnect members 23 and 25 act to bilaterally stabilize the adjacent vertebrae (in this case L3 and L4) in a position as they were located prior to the surgical procedure. In the case of disc removal and implant placement it is advantageous to have the two vertebra stabilized in a natural position so that implant selection and placement into a proper space can be facilitated.

However, the use of the conventional pedicle screws 11, 13, 15 and 17 of FIG. 1, along with the interconnect members 23 and 25 create a significant interfering structure which can block access to the intervertebral space, and also can physically interfere with any retractor system used to facilitate access to the intervertebral space. Retractor systems which operate more closely to the spine are more stable and subject to greater control by the surgical practitioner. Further, when retractor system is closer to the patient, a wider view is available, all other factors remaining the same.

FIG. 1 also illustrates that the conventional pedicle screws 11, 13, 15 and 17 have to have an insertion point and angle which will enable the conventional linear pedicle screw to travel straight through the pedicle and into the main vertebra body. This must be accomplished with minimum damage to bone tissue, and without angling into the spine, and without simply missing its path so that it emerges from the pedicle even if it continues back into the vertebra. Any opportunity to fail to fully engage bone volume results in a probability that the conventional pedicle screws 11, 13, 15 and 17 will not hold and may fail in their contribution to fix the interconnect members 23 and 25.

When it is considered that the large amounts of tissue must be removed or compromised to give the surgical practitioner the ability to locate the exact point of insertion and then to rotatably insert the conventional pedicle screws 11, 13, 15 and 17 at the correct angle, it can readily be seen that conventional pedicle screw insertion is both difficult and fraught with the possibility of error, times four. Further, because the conventional pedicle screws 11, 13, 15 and 17 have relative large diameter compared to the pedicle, the room for error which would still allow a successful insertion is reduced.

Figure 2:
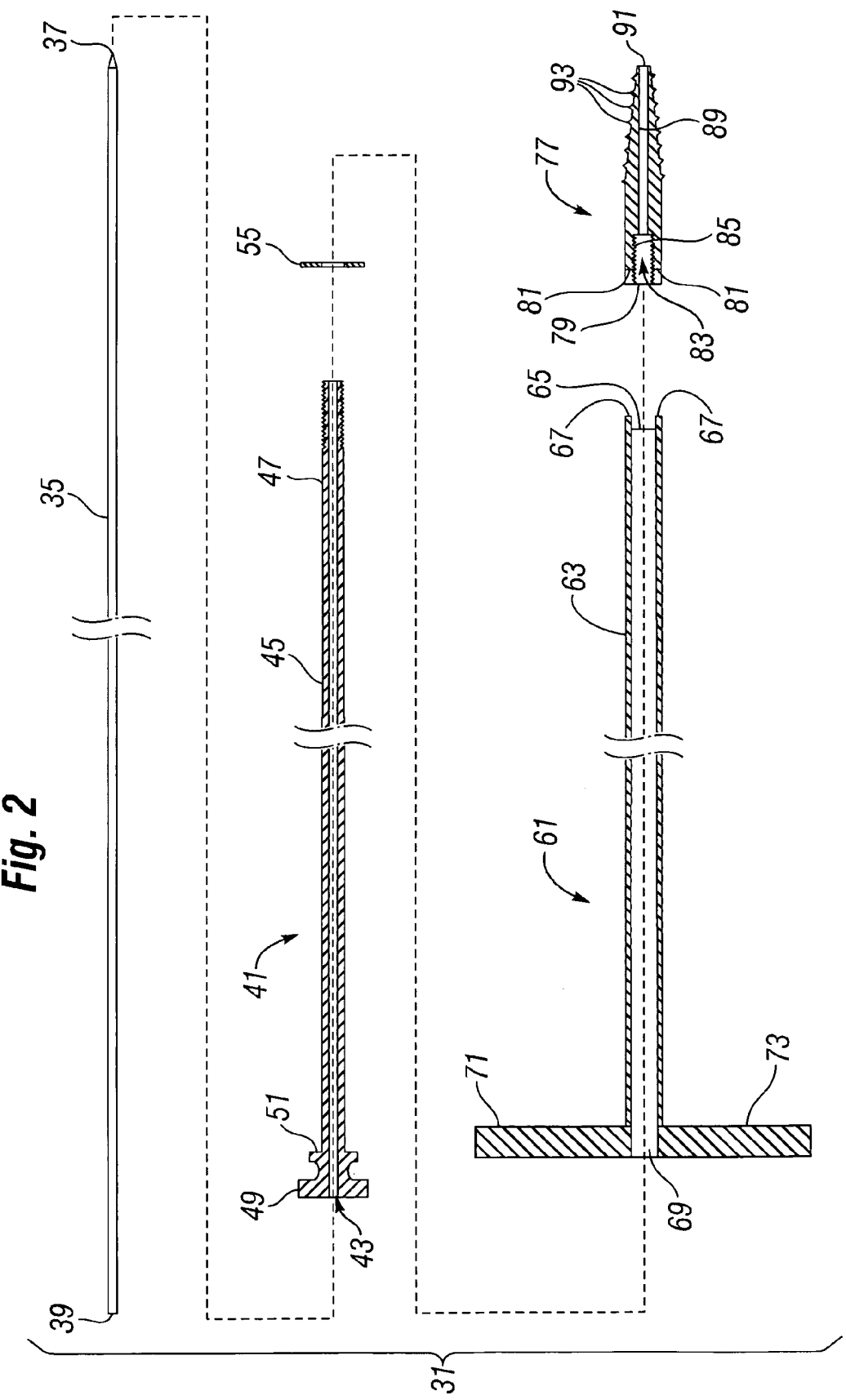
FIG. 2 is a sectional exploded view illustrating the basic components in one embodiment of a pedicle dart system.

Referring to FIG. 2, an exploded view of a pedicle dart system 31 is illustrated. A guide pin 35 is preferably a solid length of material having a sharp point 37 at one end opposite a blunt end 39. A pedicle dart fastener 41 includes a guide pin through bore 43 for enabling the guide pin 35 to easily pass through as well as to rotate. The pedicle dart fastener 41 in the embodiment shown as a main barrel 45 and a set of external threads at one end. The opposite end has an enlarged control knob 49 spaced apart from an insertion limiting land 51 to insure that the enlarged control knob 49 will be prominent and easily actuatable with regard to any type of instrumentation into which the pedicle dart fastener 41 is inserted.

It is understood that the use of external threads 47 to rotationally engage a pedicle dart (to be discussed) by threadable rotation to achieve attachment and axial movement, is but one of many ways this can be accomplished. Other ways include a quick key insertion, an external snap detent, or magnetic attraction or any other structure. The remainder of the structure will reveal that the external threads 47 will not undergo a static turning force and therefore no rotational pressure will be exerted on the external threads 47.

An optional friction washer 55 is seen for eliminating component wear and its need will depend upon the materials chosen for the pedicle dart system. Next is seen the indexed sleeve 61. Indexed sleeve 61 includes a main body 63 seen as a cylindrical barrel shaped body but need not be. Main body 63 has a terminal end 65 with a pair of fingers 67 extending beyond the terminal end 65. The indexed sleeve 61 has a central bore 69 through which the main barrel 45 of the pedicle dart fastener 41 may freely pass and rotate. A pair of handles 71 and 73 extend away from the end of the indexed sleeve 61 to facilitate manual rotation of the indexed sleeve 61 with some level of manual force.

To the right of the indexed sleeve 61, a pedicle dart 77 is shown in cross section. As will be seen, although the pedicle dart 77 can have a variety of functional structures, the pedicle dart 77 shown in FIG. 2 has a threaded conical exterior and internally threaded surfaces.

Beginning at the left, the pedicle dart 77 has a pair of fingers 79, only one of which is seen due to the cross sectional nature of the drawing. The fingers 79 of the pedicle dart 77 interlock with the fingers 67 of the indexed sleeve 41 and will ideally extend all the way to the terminal end of the indexed sleeve. An end 81 of the pedicle dart 77 defines the point that the pedicle dart 77 fingers 79 extend rearwardly of it. The ends 81 accommodate the terminal ends of the fingers 67 of the indexed sleeve 41 extending toward the pedicle dart 77 to rotationally engage it.

Pedicle dart 77 has a bore 83 having an internal threaded surface 85 which is complementary to the threaded surface 57 of the pedicle dart fastener 41. Beyond the internal threaded surface 85, the pedicle dart 77 has a guide pin bore 89 which extends through the pedicle dart 77 and opens at a tip end 91 of the pedicle dart 77. As can be seen, when the pedicle dart 77 is brought close to the end 65 of the indexed sleeve 61 such that the fingers 67 of the indexed sleeve slide past the fingers 79 of the pedicle dart 77, any rotational force applied to the indexed sleeve will be transmitted to the pedicle dart 77. Pedicle dart 77 is also seen as having an externally threaded surface 93 for boring into bone tissue. A spiral cutting thread can be used, but also other non-spiral cutting surfaces, such as a ribbed cone with tapered radiating relatively angled members for an even bore, or a conical rasp.

So long as the pedicle dart 77 is in close relationship with the indexed sleeve 61, the fingers 67 and 79 will directly transfer any turning or movement of the indexed sleeve 61 through to the pedicle dart 77. In essence, the indexed sleeve 61 becomes a long device which can have its tip member selectively attached or removed. The pedicle dart fastener 41 serves several. First it can engage or disengage the pedicle dart 77. Secondly, it can pull the pedicle dart 77 closer enough to the indexed sleeve 61 that the fingers 67 and 79 will engage each other. Third, it keeps the pedicle dart 77 and index sleeve centered to insure that the engagement of the fingers 67 and 79 are even and both rotate fully engaged around a common axis.

FIG. 2 illustrates that the guide pin 35 can be freely inserted into the guide pin bore 43 at any time and from either end of the guide pin bore 43. The guide pin 35 can be used independently with the combination pedicle dart 77, indexed sleeve 61 and main body 63 assembled as a unit. In other words, the guide pin 35 can be inserted either by gentle force or by gentle tapping to locate a point of insertion. The guide pin 35 is used as an easy-to-handle, long object which can be oriented to indicate the angle at which the pedicle dart 77 is to be inserted. Then, the combination pedicle dart 77, indexed sleeve 61 and main body 63 assembled as a unit can be guided over the blunt end 39 of the guide pin 35 and then slid along the guide pin directly to the exterior of the pedicle. A few turns of the combination of the pedicle dart 77, indexed sleeve 61 and main body 63 assembled as a unit will result in some of the externally threaded surface beginning to engage the bone tissue of the pedicle. Once insertion of the pedicle dart 77 begins, the guide pin 35 can be withdrawn while the remainder of the pedicle dart system 31 is turned to put the pedicle dart 77 fully into the bone tissue.

Once the pedicle dart 77 is fully inserted, the surgical practitioner can manually turn the enlarged control knob 49 in a direction that will back the set of external threads 47 of the main barrel 45 out of the threaded surface 85 of the pedicle dart 77. This action enables the pedicle dart 77 to begin to move forward with respect to the indexed sleeve 61 to enable the fingers 67 of the main body 63 to disengaged from the pair of fingers 79 of the pedicle dart 77. Further turning of the enlarged control knob 49 enables the pedicle dart fastener 41 to become completely disengaged from the pedicle dart 77.

The same process can be followed in reverse to re-engage the pedicle dart 77. The combination of the indexed sleeve 61 and main body 63 assembled as a unit with the indexed sleeve 61 urged forward will cause the set of external threads 47 of the indexed sleeve 61 to protrude forward of the fingers 67 and in a position to find and engage the internal threaded surface 85 of a pedicle dart 77. Turning the enlarged control knob 49 in a direction that will begin to engage the set of external threads 47 of the pedicle dart fastener 41 into threaded surface 85 of the pedicle dart 77 will begin to draw the pedicle dart 77 toward the indexed sleeve 61. Slight turning of the indexed sleeve 61 will cause the fingers 67 to assume a complementary position with respect to the fingers 79 of the pedicle dart 77, with fingers 67 and 79 sliding past each other to enable rotational re-engagement of the indexed sleeve 61 with the pedicle dart 77. This same procedure is used for both loading a new pedicle dart 77 by hand and for re-engaging a pedicle dart 77 which may have previously been implaced in bony tissue. In the latter case, once re-engaged, the indexed sleeve 61 can be used to extract the pedicle dart 77. The technique of extraction will depend upon the type of pedicle dart 77, as will be shown. Where the externally threaded surface 93 is present, turning to loosen the threads of the externally threaded surface 93 sufficient to disengage such externally threaded surface 93 will precede simple extraction.

Referring to FIG. 3, a sectional view illustrating the assembled pedicle dart system 31 is seen. The guide pin 35 is preferably much longer than the pedicle dart fastener 41 so that a sufficient length of the guide pin 35 will be available for easy manipulation. The pedicle dart fastener 41 can be withdrawn back through the main barrel 45 of the indexed sleeve 61 main body 63, and an optional structure can be present to stabilize the pedicle dart fastener 41 longitudinally with respect to the main barrel 45 of the indexed sleeve 61. Such optional structure may include a set screw extending through the main barrel 45 of the indexed sleeve 61 to engage a reduced land on the pedicle dart fastener 41, or some other spring detent can be used. Any optional structure should be configured with a mind toward facilitating sterilization of this instrument.

FIG. 4 is a plan assembled view illustrating the interfitted components of the basic pedicle dart system 31 with a further embodiment of a pedicle dart seen as pedicle dart 95. Pedicle dart 85 has conically tapering exterior ribs 97 and illustrates that the pedicle dart system 31 is not limited to an externally threaded entry into bone tissue. The conically tapering exterior ribs of pedicle dart 95 will enable more of a concentrically even wearing effect by which bone entry is accomplished. This also reduces the possibility that the adjacent tissues might be overly compressed from the action of externally threaded surface 93 combined with forward pressure applied by a surgical practitioner. In effect, the surgical practitioner can select the particular pedicle dart 77 or 95 desired for use given the bone tissue conditions.

Referring to FIG. 5, an expanded perspective view of a portion of the pedicle dart 95 is seen in a position below the terminal end 65 and pair of fingers 67 seen in previous figures. The relatively deep tapered rib section 97 is seen. Referring to FIG. 6, an end view of the pedicle dart of FIGS. 4 and 5 illustrates the geometric shape as having deep ribs, which are seen to be five in number.

Referring to FIG. 7, an expanded perspective view of a further embodiment of a pedicle dart 101 as having a tapered rib section 103, but with more shallowly formed and more numerous ribs. Referring to FIG. 8, an end view of the pedicle dart 101 of FIG. 7 illustrating the geometric shape as having shallow ribs within its tapered rib section 103, which are six in number.

Referring to FIG. 9, an expanded perspective view of a further embodiment of the pedicle dart is seen as a pedicle dart 105 as having a conical taper 107. This embodiment can be used where the bone tissue is soft or where the surgical practitioner wants only a small or force determined opening or starter aperture in the bone tissue. Referring to FIG. 10, an end view of the pedicle dart 105 of FIG. 9 illustrating the geometric conical shape taper 107.

Referring to FIG. 11 an expanded perspective view of a further embodiment of a pedicle dart 111 formed as a probe having a reduced diameter portion 113 with an optional slight small end conical taper 115. The pedicle dart 111 is especially useful with an indexed sleeve 61 used as a probe to move tissues and "feel", in addition to looking for pedicle placement. Thereafter the guide pin 35 can be employed to make an impression on the spot on the pedicle where further activity is to occur. In that case, the assembly including the indexed sleeve 61, pedicle dart fastener 41 and pedicle dart 111 can be removed from the guide pin 25, then loaded with pedicle darts 105, 95, 101 or 77 and then re-inserted over the guide pin 35 for further pedicle dart insertion activity. Referring to FIG. 12, an end view of the pedicle dart 105 of FIG. 11 is shown and illustrating the geometric stepped shape.

Figure 13:
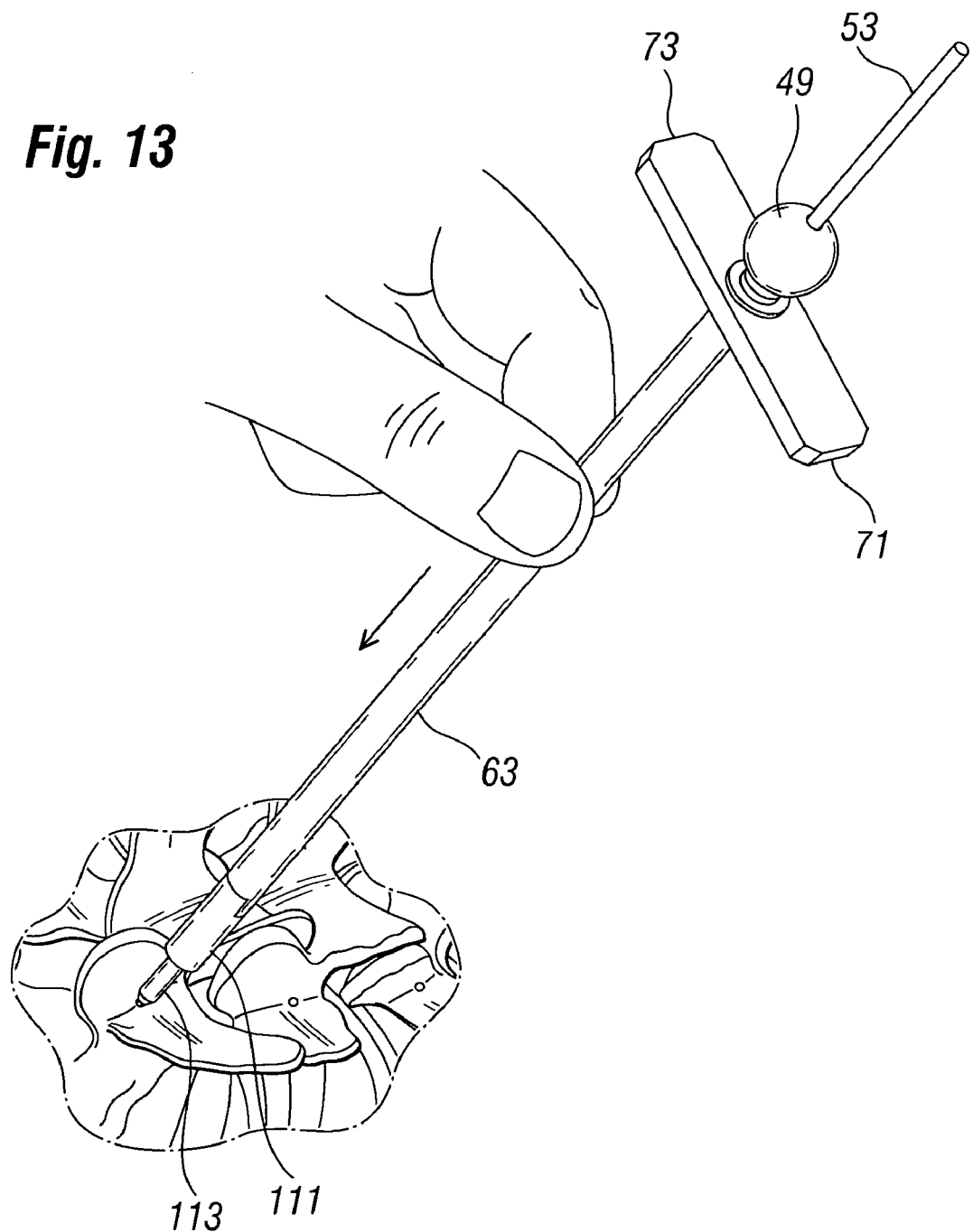
FIG. 13 illustrates the pedicle dart system configured as a probe and using the probe pedicle dart seen in FIGS. 11 and 12 with the guide pin withdrawn while using it as a probe to locate the point where the guide pin is to be inserted.

FIG. 13 illustrates the pedicle dart system configured as a probe and using the probe pedicle dart 111 seen in FIGS. 11 and 12 with the guide pin 35 withdrawn while using it as a probe to locate the point where the guide pin 35 is to be inserted. Also illustrated is a slightly differently shaped enlarged control knob 49 as having a more spherical appearance.

Figure 14:
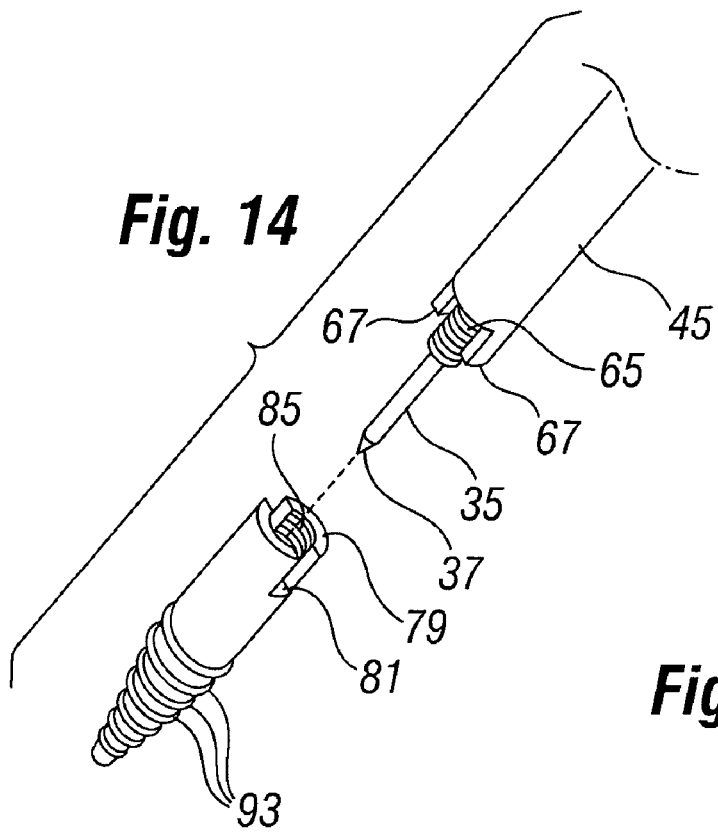
FIG. 14 illustrates an expanded perspective view of the pedicle dart of FIGS. 2 and 3 in a position to be loaded onto the end of the pedicle dart fastener and indexed sleeve.

Referring to FIG. 14, a perspective view of the pedicle dart 77 of FIGS. 2 and 3 is shown in a position to be loaded onto the end of the pedicle dart fastener, of which only the tip end having threads 47 is seen, and in which the guide pin 35 is optionally present to aid in alignment. Guide pin 35 is not required for attachment of the pedicle dart 77 but guide pin 35 insertion will automatically concentrically align the pedicle dart 77 so that the only other alignment is rotational, to align the fingers 79 with fingers 67. Fingers 79 are seen as optionally having a greater radial extent while the fingers 67 have a lesser radial extent, but this need not be the case. Further, instead of using two fingers on each component (pedicle dart 77 and the end of the main barrel 45), one finger, three fingers, or four or more fingers could be used. Note that the threaded surface 47 of the end of pedicle dart fastener 41 extends slightly beyond the most distal ends of the fingers 67 so that the internal threaded surface of the pedicle dart 77 may be engaged before the fingers 67 and fingers 79 need be rotated out of any interfering alignment.

Figure 15:
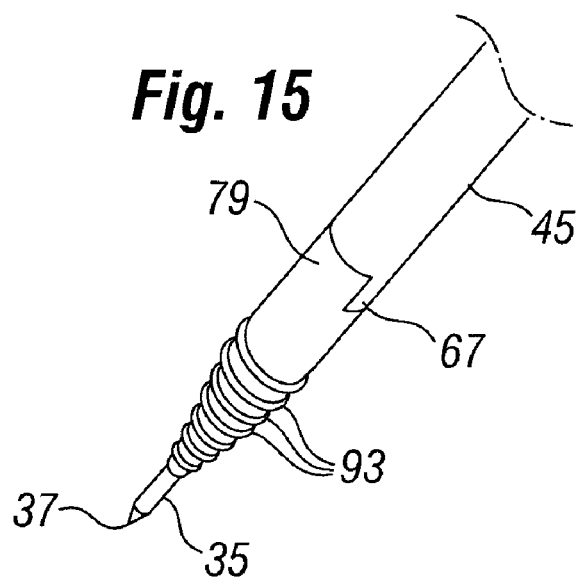
FIG. 15 illustrates an expanded perspective view of the components seen in FIG. 14 but joined to form a complete pedicle dart system assembly ready for guide pin guided implacement.

Referring to FIG. 15, a perspective view of the components seen in FIG. 14 are shown as joined to form a complete pedicle dart system 31 assembly ready for guide pin 35 guided implacement.

Figure 16:
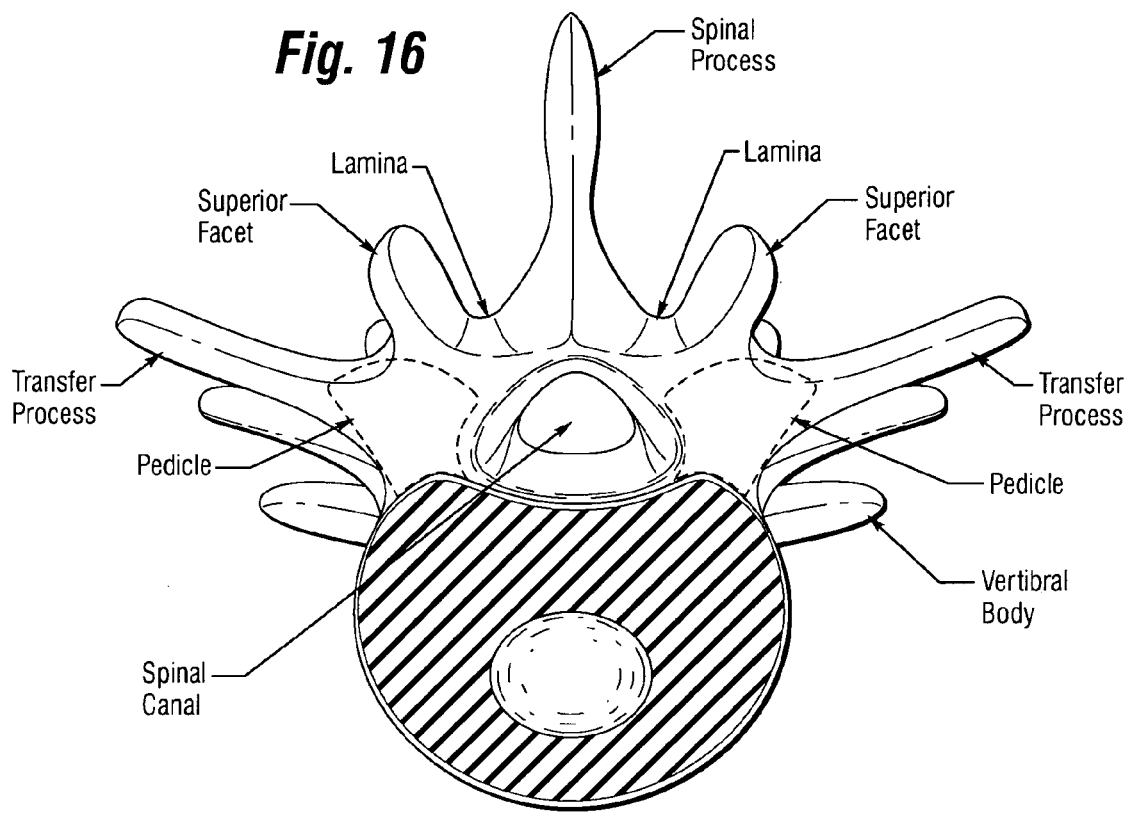
FIG. 16 illustrates a partial sectional view of a vertebra with identification of component parts and with the pedicle shown in dashed line format behind the transfer process.
Figure 17:
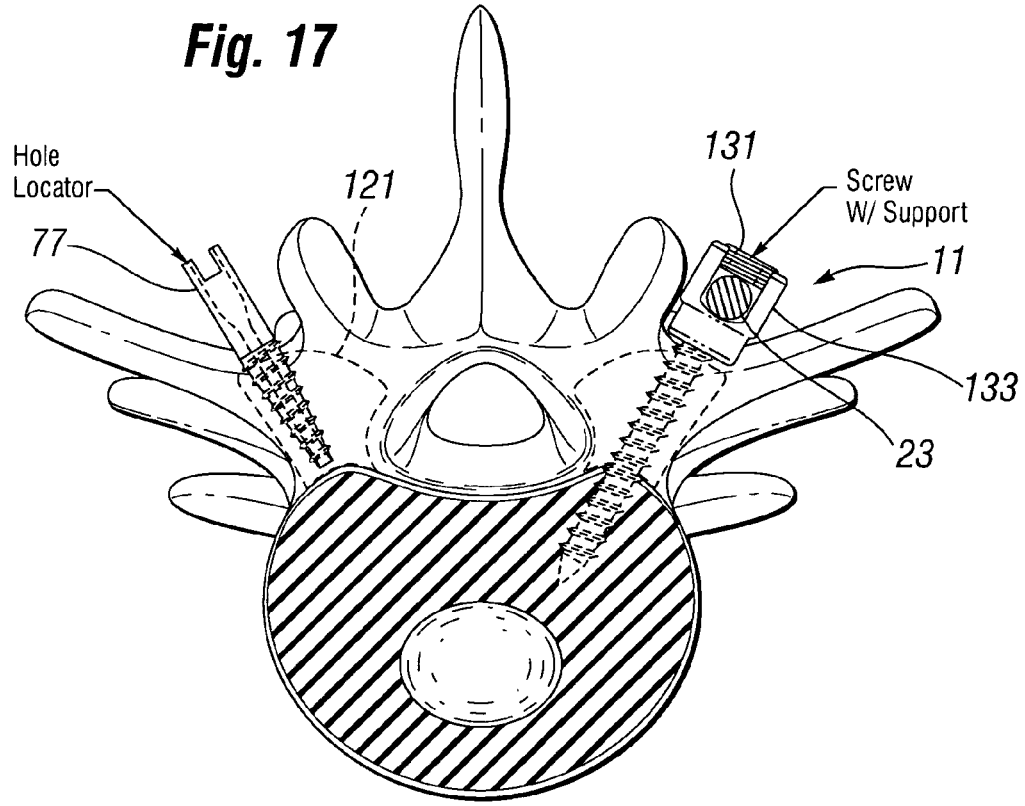
FIG. 17 illustrates insertion of a pedicle dart in comparison with the pedicle screw seen in FIG. 1 and can be used to illustrate several aspects of the differences and possibilities for cooperation between the two structures.

Referring to FIG. 16, a partial sectional view of a vertebra with identification of component parts and with the pedicle 121 shown in dashed line format behind the transfer process is given for further reference. Referring to FIG. 17, an illustration of insertion of a pedicle dart 77 is shown in comparison with the conventional pedicle screw 11 seen in FIG. 1 and can be used to illustrate several aspects of the differences and possibilities for cooperation between the two structures. The conventional pedicle screw 11 is also seen has having a compression screw 131 which operates within a housing 133 to compress the interconnect member 23.

First, it can be noted that the pedicle dart 77 is smaller and shorter than the conventional pedicle screw 11. The pedicle dart 77 is shown in a location where it has been only half way inserted into the pedicle. It can be inserted further in or less further in. Conventional pedicle screw 11 is seen as having a proud high appearance. With the conventional pedicle screw 11 the surgical view is obstructed in terms of height. The pedicle dart 77 however can go deeper into the bony mass to have a low profile appearance which interferes less with other surgical instrumentation and structures and yet still marks the angle and location. Further, the internal threaded surface 85 of the pedicle dart 77 (not seen in FIG. 17) which is used to engage set of external threads 47, can similarly be used to anchor other interconnect structure used during the operation where permissible.

However, one of the main purposes for the pedicle dart is to more easily "start" the path into the bone tissue, for both angle and location. In many operations the pedicle darts 77 may be implaced for only 30 minutes before either being removed or supplemented by other different sized structures threadably or otherwise inserted into the bone tissue, especially where greater depth, greater diameter, or other characteristics are desired. Other different sized structures may be expected to be inserted and removed by virtue of their compatibility with the pedicle dart system 31 of the invention.

Figure 18:
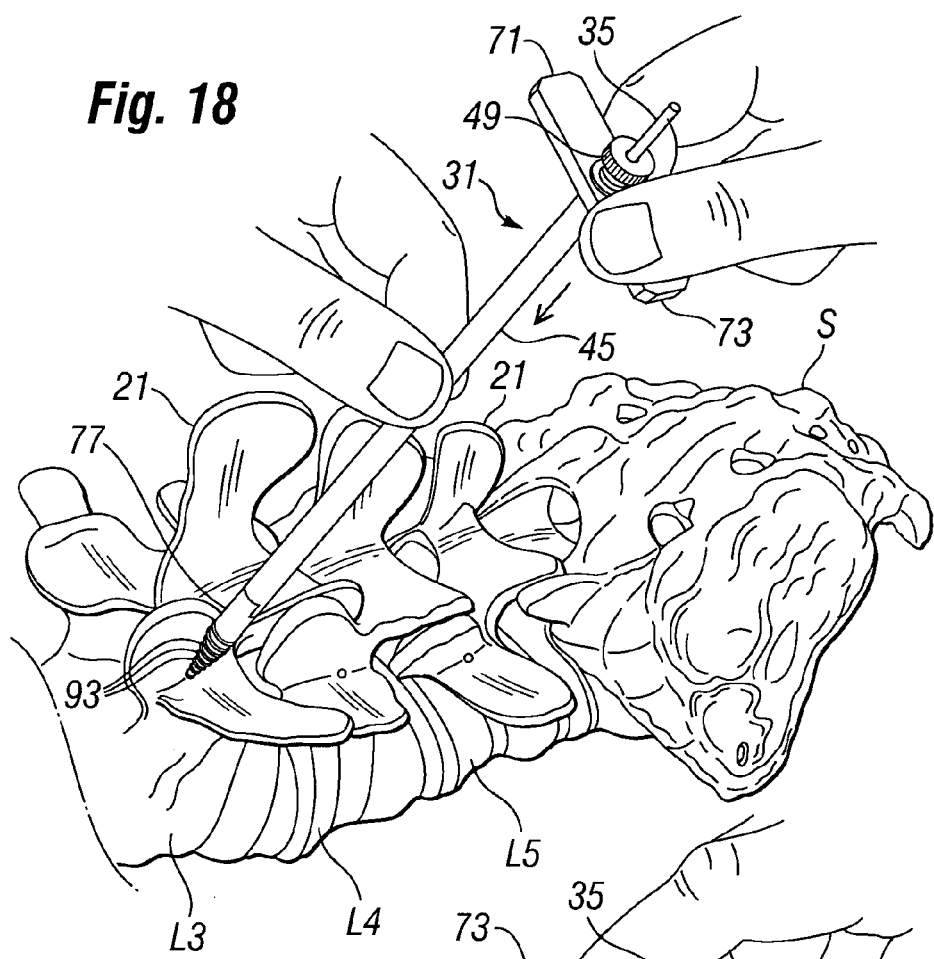
FIG. 18 is a perspective view illustrating the initial step of guide pin location and at the point in the process where the pedicle dart has translated along the guide pin and first makes contact with the pedicle.

Referring to FIG. 18. a perspective view is used to illustrate the initial step of initial contact of the pedicle dart 77 with the pedicle dart system 31 at a point in time after the guide pin 35 has used, with or without the probe configuration seen in FIG. 13, for marking location where the pedicle dart is to be inserted. It is at this time that the surgical practitioner angularly orients the pedicle dart system 31 so that further manipulation of the pedicle dart system will result in the linear entry path desired. The pedicle dart 77 is shown as being securely attached so that rotation of the indexed sleeve will result in rotation of the pedicle dart 77. The view illustrates a time just before the rotation of the components of the pedicle dart system 31 begins, with the combination pedicle dart fastener 41, indexed sleeve 61, and pedicle dart 77 translated along the guide pin 35 first making contact with the pedicle 121.

Figure 19:
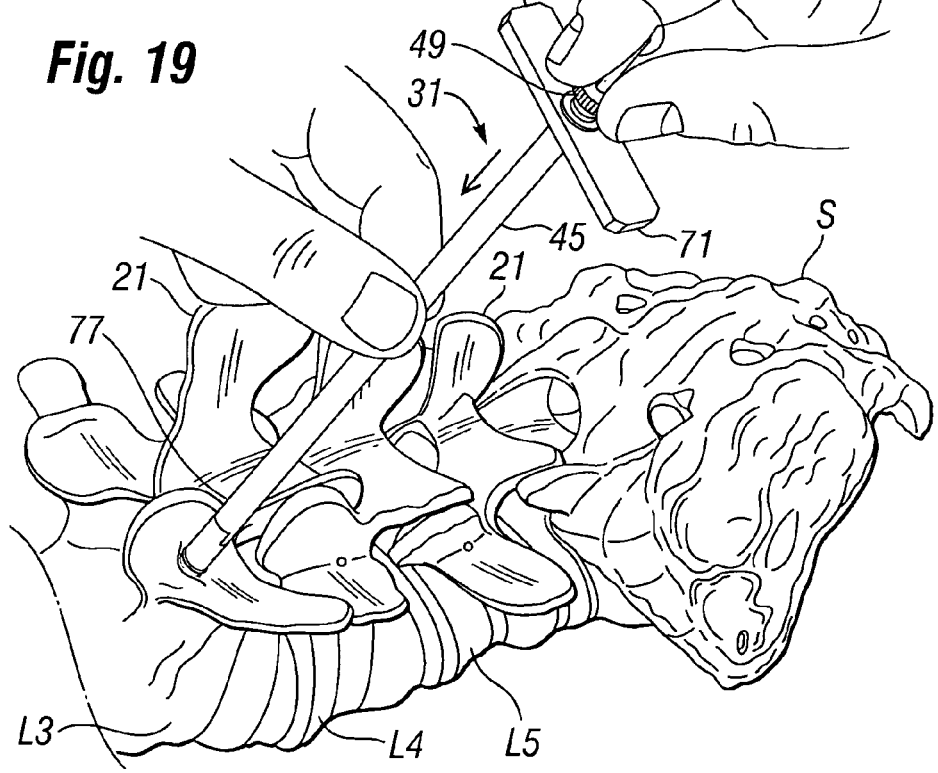
FIG. 19 is a view similar to that seen in FIG. 18 in which the pedicle dart has been inserted and at the point where the surgical user is just about to begin turning the control knob of the pedicle dart fastener to release the pedicle dart.

Referring to FIG. 19 is a view similar to that seen in FIG. 18 in which the pedicle dart has been inserted to a depth of about half of its length and at the point where the surgical user is just about to begin turning the control knob 49 of the pedicle dart fastener 41 to release the pedicle dart 77 and just after the turning operation has ceased.

Figure 20:
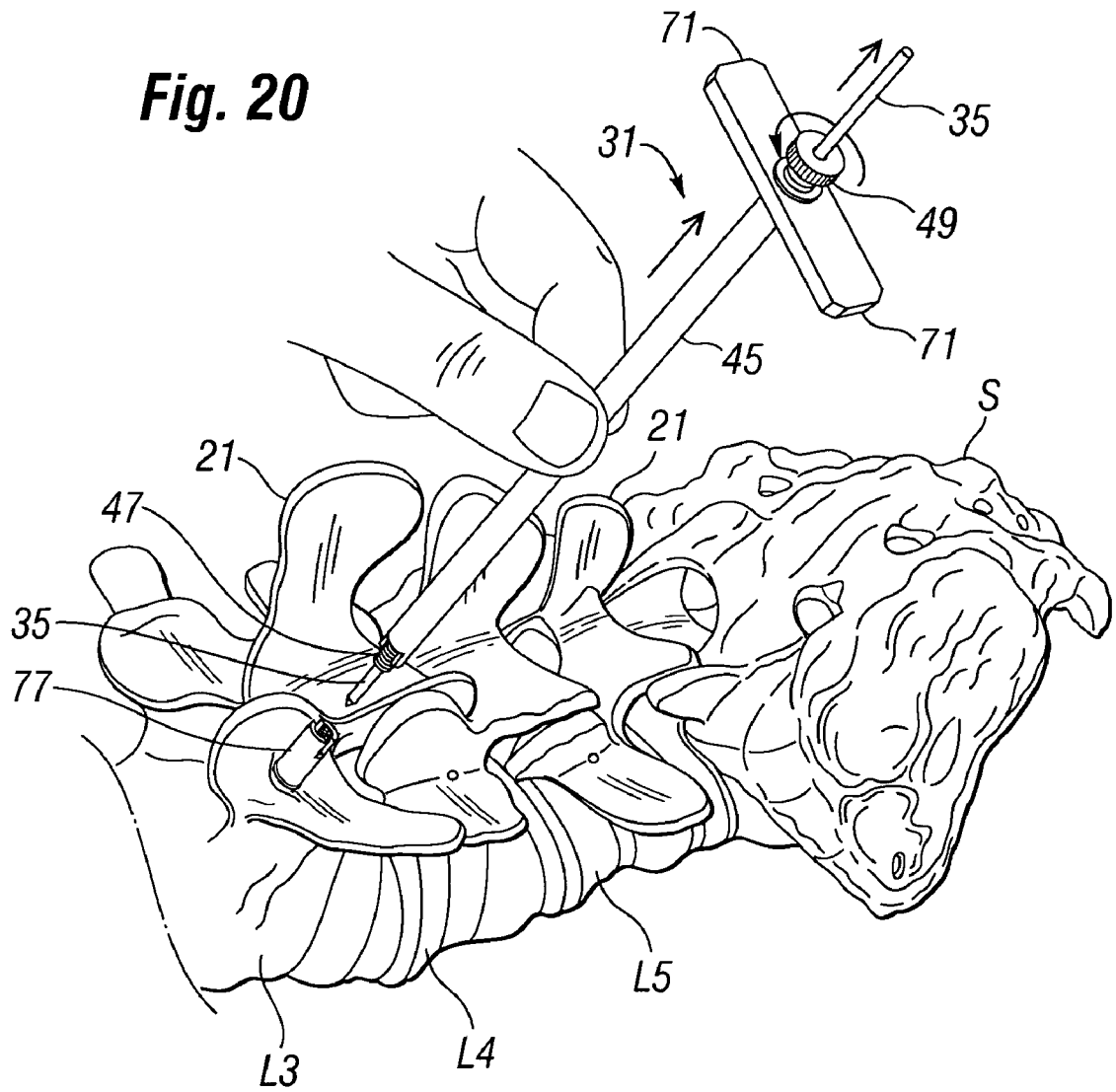
FIG. 20 is a view similar to that seen in FIGS. 18 and 19 in which the indexed sleeve and pedicle dart fastener has been decoupled from the pedicle dart and is being moved away from the surgical field.

Referring to FIG. 20, a view similar to that seen in FIGS. 18 and 19 is shown in which the indexed sleeve 61 and pedicle dart fastener 41 has been decoupled from the pedicle dart 77 and is being moved away from the surgical field. The practitioner would repeat the process of FIGS. 18-20 to insert as many pedicle darts as necessary. Ideally, the pedicle dart may be a tapered, cylindrical device having a sharp point at one end leading to self-tapping threads 93 on the outer surface for approximately 75% of its length. The opposite end is flat, and may be male or female indexed to match the female or male index, respectively on the indexed sleeve 61. The center of the pedicle dart 77 may be cannulated to accept the guide pin 35.

It is clear that the pedicle dart system of the invention can be modified to handle a wide variety of Procedures. The material used for all components of the pedicle dart system should be capable of withstanding sterilization and impact. Different materials may be employed based upon the forces and interconnection forces expected to be encountered. Although the pedicle dart system 31 can be used in many different types of surgical procedures, an example involving minimally invasive surgery transforaminal lumbar interbody fusion (MIS TLIF) will be described as one of those examples.

MIS TLIF Procedure

1. Insert any guide pin to identify the level of the lumbar disk to be removed.
2. Make a midline incision centered over the guide pin 35 appropriate for the levels of surgery to be performed, which is usually the distance from the tip of the spinous process of the levels to be fused.
3. Undermine the full thickness of the skin 2-3 cm circumferentially to allow the incision to be moved in all directions.
4. Make a fascial incision 1-2 cm lateral to the spinous processes. Insert Cobb elevator and sweep the multifidus muscle off the spinous processes and lamina and lateral to the facet joint. Insert MIS retractor with the proper blade length and shape and open the retractor blades to retract the soft tissue from the inter-laminar space. The inverted "V"-shaped space thus created allows for excellent visualization for the laminectomy/diskectomy.
5. Fasten the retractor to the universal arm attached to the surgical table to stabilize the retractor if desired.
6. Perform a facetectomy if TLIF procedure is to be performed. Take precaution not to injure the exiting root cephalad to the disk and use a dural retractor to retract the dura and traversing root medially.
7. Perform a complete diskectomy. Prepare the disk space and insert the inter body cage of choice. A more lateral Wiltse approach to be described next can be used for inserting a longer "banana" TLIF cage for safer insertion.
8. Remove the MIS retractor and make another longitudinal fascial incision on the lateral border of the Longissimus muscle. The location of this fascial incision can also be determined by the location of the pedicle darts 105, 95, 101 or 77 as visualized with the C-arm. Insert a Cobb elevator to sweep the muscle off of the transverse processes and lateral facet joints. Insert the MIS retractor of the appropriate blade length and open the retractor blades sufficient to visualize the operative area of interest. If the fascial incision appears to be too lateral, the fascial incision can be made more medially and a "true" Wiltse muscle-splitting approach can be utilized. Deploy the retractor blades cephalad-caudally. Medial/lateral retraction may be necessary. On the medial side, a hook retractor should be used, and laterally, a blade retractor would be more effective to retract the muscle.
9. Following placement of the TLIF cage, the proud head of the pedicle dart 105, 95, 101 or 77, can be engaged easily due to the indexed sleeve 61. Remove the pedicle dart 105, 95, 101 or 77. The appropriate conventional pedicle screw can then be inserted through the hole prepared by the pedicle dart, and the contoured rod can then be applied to the heads of the conventional pedicle screw. The construct can then be compressed, and the locking screws tightened over the rod. The MIS retractor is then removed.

Internal Fixation of the Opposite Side

1. Move the midline incision to the opposite side.
2. Make a longitudinal fascial incision on the opposite side to begin the Wiltse approach. Using muscle-sparing technique, strip the muscle attachments on the transverse processes. Insert the MIS retractor with the appropriate length retractor blades, and then open the blades Cephalad-Caudally to expose the heads of the pedicle dart 105, 95, 101 or 77. Deploy medial/lateral retractor as required for sufficient exposure. Decorticate the transverse processes and lateral surface of the facet joint. Remove the pedicle dart as described before and replace with the final conventional pedicle screw 11. Insert the appropriate interconnect member 23 into the conventional pedicle screw head housing 133; then compress and tighten the locking screws 131. Apply bone graft to the decorticated posterolateral gutter, then remove MIS retractor. Suture the fascial incisions with appropriate suture material of choice and close the wound in the usual fashion.

Referring to FIG. 21, an exploded view of a second embodiment seen as a one step entry pedicular preparation device 201 and which includes a pedicle dart 205 having a proximal end 207, a tapered threaded section 209, a cylindrical section 213, a frusto conical expansion section 217 and an engagement sleeve 219. The engagement sleeve 219 has a "T" shaped slot 221, and a distal open end 225.

Just above the distal open end 225 of the pedicle dart 205 is a main barrel 231 having a main body 233, proximal end 235 and a distal end 237. The proximal end 235 has a block 239 to enable turning force registration. Above the block 239, a threaded member 241 is seen as having a main barrel bore 243 which will accommodate a guide pin (to be discussed). Near the proximal end 235 of main body 233, a spring urged ball detent 245 is seen just above a protruding key 247. The protruding key 247 is simply a post which may extend radially from the body 233 at a right angle. The protruding key 247 can be a threaded insert or it can be formed integrally with the body 233.

The block 239 will selectably engage with a bar 249 which will serve as an impact bar or a manual turning bar, or both. The ability to remove and substitute manipulation and other structures onto the body 233 may be found by the surgical practitioner to be a valuable capability. In other embodiments to be shown, the manipulation structure may be fixed to the body 233. The characteristic of modularity can enable the surgical practitioner to further substitute and customize the instrument to many specialized needs and capabilities. The bar 249 has a central aperture 251 to permit a lower protrusion 253 of a thumbscrew 255 to fit through it to engage with the threaded member 241. The lower protrusion 253 has internal threads (not shown in FIG. 21) which engage the threaded member 241. The thumbscrew 255 has an upper bore 257 to accommodate the guide pin (to be discussed). The main barrel 231, main body 233 and bar 249 forming a manipulator 269.

To the right of the pedicle dart 205 and barrel 231, a guide pin 261 is seen. Guide pin 261 has a central body 263 having a sharp pointed first end 265 and a flat second end 267. Regardless of whether the pedicle dart 205 is engaged onto the main barrel 231, the guide pin 261 can pass completely through both of these structures. This enables the main barrel 231 and its distal assembly, including the bar 249 and thumbscrew 255 to be assembled and disassembled either while on the guide pin 261, while not on the guide pine 261. This enables the guide pin 261 to be used initially, followed by manipulation of the pedicle dart 205 by the main barrel 231, and the ability to leave the pedicle dart 205 in place either surrounding the guide pin 261 or with guide pin 261 removed.

As can be seen by the alignment shown in FIG. 21, the guide pin can pass through the thumbscrew 255, into the central aperture 251, main barrel 231 and pedicle dart 205 and passing completely through and free of the pedicle dart 205 through the proximal end 207 of the pedicle dart 205, as will be more fully shown. Also seen by the alignment shown in FIG. 21, the proximal end 235 of the main body 233 of the main barrel 231 can enter the distal open end 225 of the engagement sleeve 219 only when the protruding key 247 is in alignment with the "T" shaped slot 221. Once the alignment of the protruding key 247 with the "T" shaped slot 221 is hand, the proximal end 235 of the main body 233 of the main barrel 231 can continue to enter the distal open end 225 of the engagement sleeve 219, but only until the protruding key 247 reaches the end of the "T" shaped slot 221.

Referring to FIG. 22, an assembled view of the second embodiment seen in FIG. 21 illustrates the point at which the protruding key 247 reaches the farthest extent into the "T" shaped slot 221. At this point, as will be shown, the main body 233 of the main barrel 231, with its the protruding key 247 can be turned in either direction with respect to the "T" shaped slot 221. Once the protrusion 231 is turned to one side of the "T" shaped slot 221 or the other, it falls out of alignment with the main entry portion of the "T" shaped slot 221 and the main body 233 of the main barrel 231 cannot be directly withdrawn from the engagement sleeve 219. Only upon re-alignment of the protrusion 231 to the middle of the "T" shaped slot 221, can the main body 233 of the main barrel 231 be withdrawn from the engagement sleeve 219 to thereby disconnect the pedicle dart 205 from the main barrel 231.

This means that so long as the practitioner is even slightly urging the main barrel 231 in one direction or the other, the pedicle dart 205 will not become disengaged from the remainder of the structures of the one step entry pedicular preparation device and system 201. This means that the surgical practitioner can turn the one step entry pedicular preparation device and system 201 to the right and urge it forward or rearward, or that the surgical practitioner can turn the one step entry pedicular preparation device and system 201 to the left and urge it forward or rearward without worrying about disengagement of the pedicle dart 205.

If, however, the main barrel 231 is turned slightly from a clockwise or counterclockwise turned position, and while simultaneously placing a rearward pull on the main barrel 231, the protruding key 247 will "find" the center of the "T" shaped slot 221 and it will then be possible to back the main barrel 231 out of engagement with engagement sleeve 219 of the pedicle dart 205. Since the one step entry pedicular preparation device and system 201 will be used by naturally turning it with the hand while pushing or withdrawing it, especially by manipulation of the bar 249, the surgical practitioner will always be selectably and controllably connected with the pedicle dart while manipulating it. Further, disconnection would only be had by turning the main barrel 231 in one direction, sufficient that the protruding key 247 contact one side of the "T" shaped slot 221, then putting gentle rearward force on the main barrel 231 as the main barrel 231 is rotated in an opposite direction. Only then will the protruding key 247 "finds" or contacts the center of the "T" shaped slot 221. Even more importantly, whether manipulating or disengaging, the surgical practitioner will have full and clear view of the protruding key 247 and the "T" shaped slot 221, especially as it rotates. Surgical practitioners will be able to quickly pickup the "feel" of operation of the one step entry pedicular preparation device and system 201 after only a few engagements and disengagements of the pedicle dart 205.

FIG. 23 is a closeup view of the second embodiment of the pedicle dart 205 and its interaction with the end of the main barrel 231 and illustrating the engagement projection or protruding key 247. Arrows indicate how the protruding key 247 enters "T" shaped slot 221, and once inserted to the fullest extend of the main opening of the "T" shaped slot 221 it can move across the main opening to the left or to the right to enable the main barrel 231 to maintain engagement with the pedicle dart 205 by engagement with the engagement sleeve 219. Also seen closeup is the threaded section 209 and the spiral thread 275 carried on a tapered section 277.

Referring to FIG. 24, a sectional view of the one step entry pedicular preparation device 201, seen in FIGS. 21-22, illustrates the cooperative relationship of the components making up the device. As can be seen, the central aperture 251 of the thumbscrew 255 leads to a thumbscrew bore 281. The thumbscrew bore 281 leads and is in communication with the bore 243 of the threaded member 241. The bore 243 of the threaded member 241 leads to a main barrel bore 285. The main barrel bore 285 is in communication with a pedicle dart 205 guide pin through bore 287 at the center of the pedicle dart 205, and which opens at the proximal end 207. As can be seen, all of these aligning bores allow the guide pin 261 to pass completely through the other assembled components of the entry pedicular preparation device 201.

Also seen, adjacent the proximal end 207 of the pedicle dart 205, is an opening 289 through which the pointed first end 265 of guide pin 261 can emerge, or through which the flat second end 267 may enter when the non-guide pin one step entry pedicular preparation device 201 is placed onto an already-in-place guide pin 261 such as to load the pedicular preparation device 201 onto a an already-in-place guide pin 261. Note the size of the opening 289 with respect to the overall proximal end 207 of the pedicle dart 205. This configuration presents a radially relatively thin metal area profile in a forward direction. This means that the pedicle dart 205 overall proximal end 207 will be able to easily begin to fit between the guide pin 261 and any bone volume into which the guide pin 261 is inserted, in order to begin threaded entry into the bone mass.

Referring to FIG. 25, a sectional view illustrating the detail taken along line 25-25 of FIG. 24 illustrates better view of a torque transmission block 239 and its keyed entrapment within the t-handle support 249. As can be seen, all of the torque from any turning movement will be transmitted from the t-handle support 249 to the block 239 via a complementary block structure 291 on the inside of the t-handle support 249. As such, the threaded member 241 only need serve to engage the thumbscrew 255 to cause the t-handle support 249 to be urged downwardly so that the block 239 and complementary block structure 291 remain engaged. It is expected that the thumbscrew 255 will only be disengaged from the threaded member 241 either for disassembly and cleaning of the one step entry pedicular preparation device and system 201, or for substitution of some other structure in place of the bar 249 making the system 201 highly modular.

Referring to FIG. 26, an expanded view of one possible set of structures and an interaction of a detent ball and spring which can help provide a more stable bi-positional force threshold for the protruding key 247 and "T" shaped slot 221 so that the protruding key 247 will not disengage the "T" shaped slot 221 unless the surgical practitioner affirmatively elects such action, by providing a withdrawing force on the manipulator 269 to overcome the holding force of the spring urged ball detent 245, is shown. As can be seen with the configuration seen in FIGS. 21 and 22, the surgical practitioner will need to keep slight forward force on the main body 233 whenever the practitioner is not actively engaged in deliberately rotating the main body 233 in one direction or the other, especially after insuring that the protruding key 247 is engaged at the two terminal ends of the "T" shaped slot 221. Such insuring verification can be by visual inspection of the protruding key 247 in the "T" shaped slot 221 or by "feeling" some resistance to turning of the pedicle dart 205 to turning when it is engaged with bone tissue or when it is otherwise frictionally engaged.

The main potential for accidental dis-engagement of the protruding key 247 from the T" shaped slot 221 is where the it is traversing main entrance of the T" shaped slot 221 as the protruding key 247 moves from one end of the horizontal part of the "T" to the other. One structure and method for preventing this is to provide some trapping force which must be overcome to remove the protruding key 247 back out of the T" shaped slot 221 when it is aligned with the main entry branch of the T" shaped slot 221. This is done by providing a raceway 295 about the inside of the engagement sleeve 219 for engaging the spring urged ball detent 245 within the raceway 295. For illustration purposes, the raceway 295 is seen as being continuous about the inside of the engagement sleeve 219, however, the restricted entry of the main body 233, coupled with a finite length of the length of the horizontal portion of the inside of the engagement sleeve 219 length of the T" shaped slot 221 will limit the path of travel of the spring urged ball detent 245 within the raceway 295 and thus the raceway 295 can have a more limited extent length. Further, a detent ball spring 297 is seen within a detent bore 299.

FIG. 27 is a sectional view as was seen in FIG. 26, but with the main body 233 shown detached from engagement with the pedicle dart 205 to give a better view of the details of the inside of the upper engagement sleeve 219 of the pedicle dart 205. The raceway 295 is seen, as is an optional chamfer 301 at the top of the engagement sleeve 219 to assist entry of the main body 233 into the engagement sleeve 219. The optional chamfer 301 leads to a central bore 305. The portion of the "T" shaped slot 221 seen in FIG. 27 is any portion which is not vertically below the main portion of the "T" shaped slot 221, that is, to one side or the other side of "T" shaped slot 221 and away from the main entry portion of the "T" shaped slot 221.

Referring to FIG. 28, a view looking directly into the "T" shaped slot 221 illustrates the action and location of the protruding key 247 and the positions it can occupy within the "T" shaped slot 221. The protruding key 247 is shown in Three positions, two of which are in phantom. The uppermost phantom view of the protruding key 247 shows the position of the protruding key 247 at the point where it is entering or exiting from the "T" shaped slot 221. The protruding key 247 shown in phantom at the main horizontal part right most position of the "T" shaped slot 221 illustrates a position in which the main body 233 is stably turning the pedicle dart 205 in a counterclockwise direction such as would occur when the pedicle dart 205 is being threadably removed from a bone. The protruding key 247 shown not in phantom at the main horizontal part left most position of the "T" shaped slot 221 illustrates a position in which the main body 233 is stably turning the pedicle dart 205 in a clockwise direction such as would occur when the pedicle dart 205 is being threadably inserted into bone tissue.

Referring to FIG. 29, a perspective view illustrates the one step entry pedicular preparation device 201 of the invention with an elongate and angularly raised handle member 311 and with a navigation structure 315 having a barrel portion 317 attached or preferably integral with a thumbscrew portion 319. It is understood that angularly raised handle member 311 and bar 249 are but two of hundreds of configurations of handle members which can be modularly substituted on system 201 or any of the systems of the invention where possible.

The navigation structure 315 can be any commercially available navigation guide, such as FluoroNav®. Most fluoroscopic navigation systems use a specifically configured support structure 321 supporting a series of possibly visually locatable or recognizable structures 323 of sufficient number and location sufficient to reliably indicate to some computational device the orientation and location of the one step entry pedicular preparation device and system 201 and thus the pedicle dart 205. As such the recognizable structures 323 are spatially machine recognizable. A navigation system typically registers an instrument to some tomographic image of the patient to allow a more exacting positioning of an instrument into the body of the patient.

The specifically configured support structure 321 supporting a series of structures 323 are shown as supported by a central block 325. Central block 325 may also have a guide pin aperture 327 leading into a bore (not shown) in communication with the thumbscrew bore 281 in the thumbscrew portion 319, with structures farther away from the thumbscrew portion 319. The provision of an angularly raised handle member 311 enables the practitioner to better manipulate the one step entry pedicular preparation device and system 201 where a navigation structure 315 might otherwise interfere with a good manual engagement with any structure, such as the bar 249. The structure from the thumbscrew portion 319, through the barrel portion 317, and navigation structure 315 can be interchanged on the one step entry pedicular preparation device and system 201, whether or not the bar 249 or the angularly raised handle member 311, or some other manipulation structure is utilized. Where the navigation structure 315 is optical it is preferable that the surgical practitioners hands not be engaged above any of the series of possibly visually locatable, machine locatable or otherwise recognizable structures 323.

Referring to FIG. 30, a further embodiment of the one step entry pedicular preparation device and system seen as a system 325 seen in assembled view, and also with a further embodiment of a guide pin 327 having a tip end 329 whose forward extent is limited by a cylindrically shaped stop 331 at the opposite end of the guide pin 327. A further embodiment of a pedicle dart 335 is shown and having a new internal mechanism (not shown in FIG. 30) which, along with a new mechanism at the end of main body 333, will enable a different engagement and disengagement procedure. Pedicle dart 335 has many of the same features seen with respect to pedicle dart 205, including proximal end 207, tapered threaded section 209, cylindrical section 213, frusto conical expansion section 217, engagement sleeve 219, distal open end 225 (not directly seen in FIG. 30). However, pedicle dart 335 lacks the "T" shaped slot 221, and the main body 333 has no protruding key 247 of pedicle dart 205. A bar 337 is seen adjacent a thumbscrew 339 similar to the location of thumbscrew 255 adjacent the bar 249 previously shown, but a new hexagonal engagement structure will be further shown.

Figure 31:
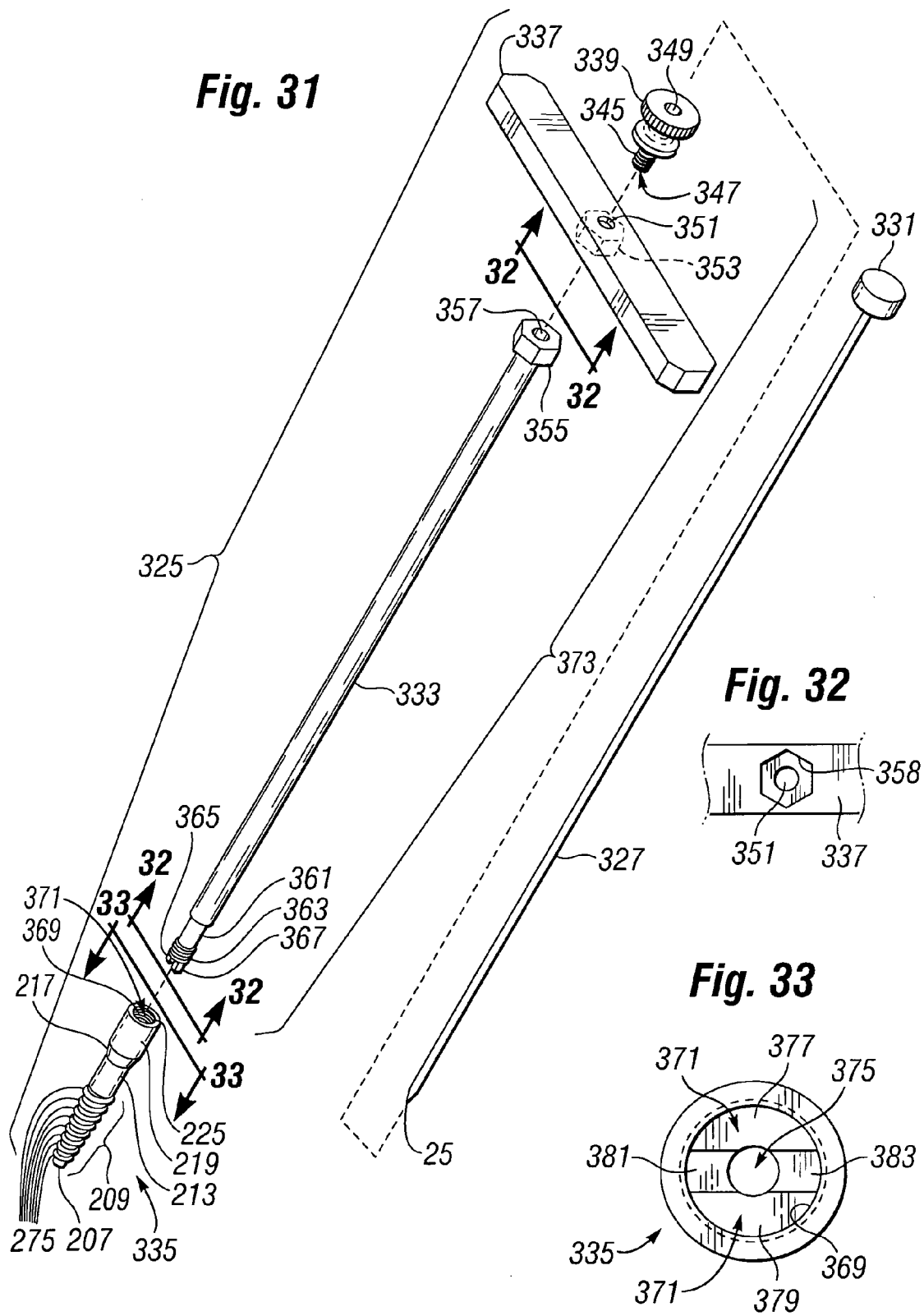
FIG. 31 illustrates an exploded view of the one step entry pedicular preparation device and system seen in FIG. 30 and begins to illustrate the structures and method of engagement of the pedicle dart.

Referring to FIG. 31, an exploded view of the one step entry pedicular preparation device and system 325 seen in FIG. 30 reveals new structures not previously seen. From the guide pin 327, the thumbscrew 339 is seen to have a threaded projection 345 with a bore 347 indicated by arrow, and in addition to a central aperture 349 which was obscured by the cylindrically shaped stop 331 seen in FIG. 30. Bar 337 has an aperture 351. Underneath aperture 351 and shown in phantom, bar 337 has a hexagonal shaped void 353.

Below the bar 337, the main body 333 is seen as having a hexagonal head 355 with an opening 357 sufficient to accept the guide pin 327. The bore 347 within the threaded projection 345 is also sized to accept the guide pin and thus the aperture 351 will be larger, so as to accommodate the outer diameter of the threaded projection 345. The hexagonal head 355 fits within the hexagonal shaped void 353 to insure that the main body 333 will turn with the turning of the bar 337.

At the proximal end of the main body 333, a reduced diameter portion 361 is seen beyond the main diameter of the main body 333. Then further proximal with respect to the reduced diameter portion 351 is a threaded section 363, Further proximal to the threaded section 363 are a pair of fingers 365 and 367 which will ideally have an outermost extent which has a diameter less than the effective diameter of the threaded section 363. The proximal end of the main body 333, including the reduced diameter portion 361, threaded section 363, and fingers 365 and 367 are seen in this exploded view and were not seen in the assembled view of FIG. 30, and are not in view when the pedicle dart 335 is engaged onto the proximal end of the main body 333.

Some additional detail of the pedicle dart are also visible in FIG. 31, including a set of internal threads 369 which extend from a point very close to the distal open end 225 of the pedicle dart 335 and into a bore 371 which contains a number of features (to be shown). Internal threads 369 are abbreviated in terms of their axial extent into the bore 371. The combination of main body 333 and its structures, including bar 337 and thumbscrew 339 form a manipulator 373.

Figure 32:
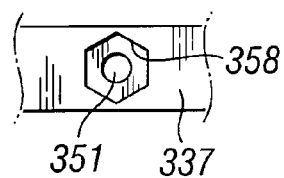
FIG. 32 is an expanded underside plan view of underside of the interchangeable bar of the distal end of the one step entry pedicular preparation device and system taken along line 32-32 of FIG. 31 and illustrating details of a hexagonal engagement system.
Figure 33:
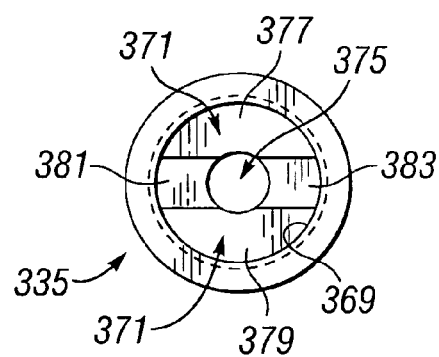
FIG. 33 is a view taken along line 33-33 of FIG. 31 and illustrates further internal details of the rotational engagement of the pedicle dart with respect to the manipulator.

Referring to FIG. 32, a view taken along line 32-32 of FIG. 31 illustrates a view of the underside of the bar 337 and better illustrates the bar 337, aperture 351 and hexagonal shaped void 353. Referring to FIG. 33, a view taken along line 33-33 of FIG. 31 illustrates further internal details of the pedicle dart 335. Most prominently at the center of pedicle dart 335 is a guide pin through bore 375 which extends through the proximal end 207. The bore 371 extends downwardly to a pair of walls 377 and 379 which are opposite each other and which form shapes having an arced exterior periphery and where the guide pin through bore 375 partially extends into the area of the pair of walls 377 and 379.

The pair of walls 377 and 379 are adjacent a pair of depressions 381 and 383. The depressions 381 and 383 have a greater depth with respect to the distal open end 255 of the pedicle dart 335 than the pair of walls 377 and 379. As will be shown, when the fingers 365 and 367 are enabled to extend below the level of the walls 377 and 379 and at least partially within the space bounded by the depressions 381 and 383, that the fingers 365 and 367 can rotationally engage the material beyond the walls 377 and 379 adjacent the depressions 381 and 383 to enable the main body 333 to impart rotational force to the pedicle dart 335. This action will be better and more fully shown in the subsequent figures. Also seen is the set of internal threads 369 seen as a dashed line representation.

Referring to FIG. 34, a view taken along line 34-34 of FIG. 31 is seen. As can be seen, the body 33 is the outermost peripheral structure seen with the next most inboard structure being the threaded section 363. The fingers 365 and 367 are seen on either side of the main barrel bore 285. The transition from fingers 365 and 367 back to the threaded section 363 can be of any shape which will not block the access of the threaded section 363.

Referring to FIG. 35, a sectional view of the one step entry pedicular preparation device and system 325 seen in FIGS. 30-34 is shown. Referring to FIG. 36, an expanded view taken along line 35-35 of FIG. 34 is seen. The left side of FIG. 34 and all of FIG. 35 serve to illustrate further details of the attachment of the bar 337. As can be seen, the threaded exterior of the threaded projection 345 only serves to bring the hexagonal head 355 far enough within the hexagonal shaped void 353 for a secure fit and which will cause the bar 337 and main body 333 to turn together. Similar to that for body 233, main body 333 includes a main barrel bore 285.

Referring to the right side of FIG. 35 and to FIGS. 37-42, a series of views and explanation of how the one step entry pedicular preparation device and system 325 makes a secure and controllable connection with the pedicle dart 335. In FIG. 34 it can be seen that the bore 371 is has a length which is longer than the length of the internal threads 369. Further, the combined length of the reduced diameter portion 361, and fingers 365 and 367 and threaded section 363 will be at least the length of the bore 371 from the proximal end 235 of the pedicle dart 335 to the pair of depressions 381 and 383 so that the fingers 365 and 367 can fit adjacent the pair of depressions 381 and 383 after the threaded section 363 has threadably passed through and beyond the set of internal threads 369 and when the practitioner urges main body 333 forward. In gently urging main body 333 forward, some turning of the body 33 may occur to enable the fingers 365 and 367 to fit within and seat in the pair of depressions 381 and 383.

This results in some axial "play" inside the pedicle dart 335 such that the main body 333 can be very gently urged in the distal direction to bring the rearward most thread of threaded section 363 into touching contact with the forward most thread of set of internal threads 369 at a point where the fingers 365 and 367 clear in the pair of depressions 381 and 383 and can freely turn in front of the pair of walls 377 and 379 and pair of depressions 381 and 383.

If the main body 333 is urged only gently forward, perhaps with some slight turning of the main body 333, the fingers 365 and 367 may slide against the pair of walls 377 and 379 and then drop forward into the pair of depressions 381 and 383. Once fingers 365 and 367 drop forward into the pair of depressions 381 and 383, the pedicle dart 335 will be rotationally fixed with respect to the main body 333. When this occurs, movement of the bar 337 can be used to rotate the pedicle dart 335.

Figure 37:
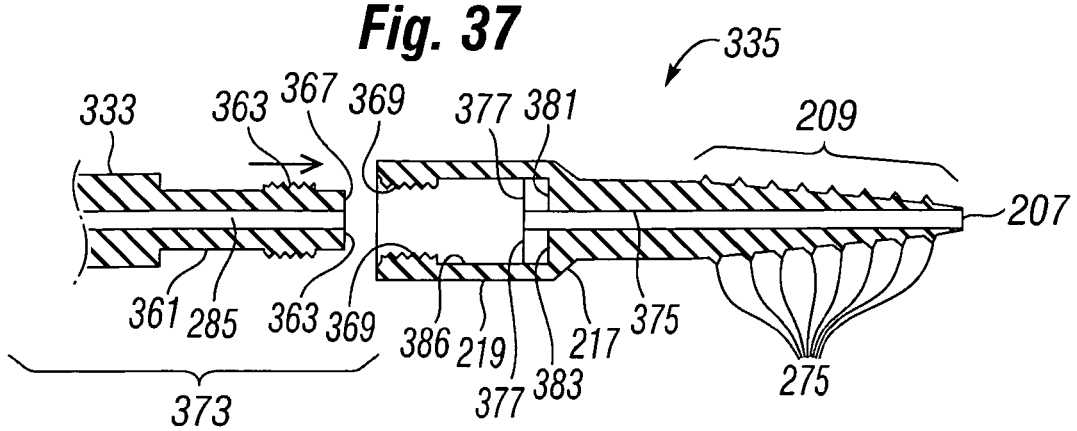
FIG. 37 is an expanded view taken along line 36-41 of FIG. 34 and illustrates the manipulator in a position just before it makes engaging contact with the pedicle dart.

Referring to FIGS. 37-44, the complete series of steps for loading a pedicle dart 335 onto the main body 333 of the manipulator 373, then using the manipulator 373 to insert the pedicle 335 into bone tissue and then detaching the pedicle dart from the manipulator 373. Referring to FIG. 37, the proximal end of a manipulator 373, including the fingers 365 and 367, threaded section 363, and reduced diameter portion 361 is brought near the pedicle dart 335. Since a side sectional view is illustrated, and since it has been emphasized that a little rotation may be necessary to have the fingers 365 and 367 find their respective pair of depressions 381 and 383. For clarity, fingers 365 and 367 will be shown aligned vertically, one over the other, while the pair of depressions 381 and 383 will be shown located vertically one over the other, and no positional deviation from this, even where rotation occurs, in order that the illustration is clear. Proximal of the set of internal threads 369 is a chamber having smooth walls 385.

In FIG. 37, as the manipulator 373 approaches the pedicle dart 335, the pedicle dart 335 may be supported by the practitioner's hand. As the manipulator 373 is brought forward, the fingers 365 and 367 enter just inside and partially slide past the beginning of the set of internal threads 369. As the forward thread of the threaded section 363 makes contact with the most distal thread of set of internal threads 369, and as the main body 333 is turned, the threaded section 363 engaged the set of internal threads 369.

Figure 38:
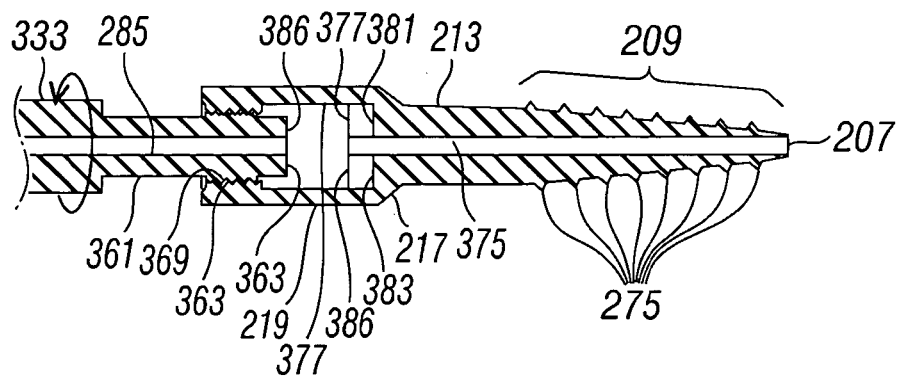
FIG. 38 illustrates the proximal end of a manipulator and pedicle dart in a position where the threaded members are in the middle of threaded engagement.
Figure 39:
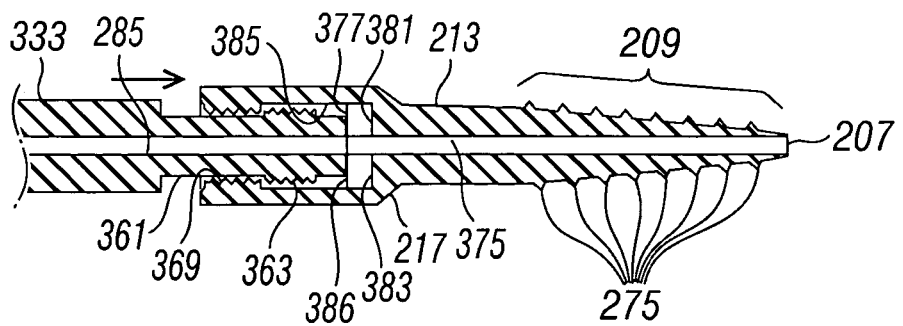
FIG. 39 illustrates a view which shows the threaded structures of the manipulator and pedicle dart having been fully attachably engaged with the pedicle dart in a position where it cannot be removed without a forward movement of the pedicle dart with respect to the manipulator (or rearward movement of the manipulator with respect to the pedicle dart) followed by turning of the pedicle dart with respect to the manipulator, but before rotational locking has occurred, the manipulator shown at the rearmost position within an abbreviated axial length of travel where the manipulator can move out of rotational locking engagement and into rotational locking engagement with the pedicle dart, the rearward most position being the out of rotational locking engagement position.

Referring to FIG. 38, this view shows the threads 369 and 363 fully engaged. As the manipulator 373 continues to turn, the threaded section 363 moves past the set of internal threads 369. Referring to FIG. 39, the threads 363 are shown as having just moved past and having just disengaged internal threads 369, but with the most distal thread of the threaded section 363 still making contact with the most proximal of the internal threads 369. In this position, pedicle dart 335 can move over an abbreviated axial length with respect to said main body 333. In this position, it can be seen that the fingers 365 and 367 can move forward by a distance slightly more than the distance between walls 377 and 379 (with only wall 377 visible in FIG. 39) and depressions 381 and 383. In FIG. 39 the main body 333 can freely slide forward and backward with respect to the pedicle dart 335, so long as the fingers 365 and 367 are oriented directly in front of the depressions 381 and 383. In the event that the fingers 365 and 367 are not oriented directly in front of the depressions 381 and 383, a gentle no resistance turning of the main body 333 will cause an alignment such that the main body 333 can move forward. Almost any forward movement will seat the fingers 365 and 367 into the depressions 381 and 383 so that any force rotation of the main body 333 will be transmitted to the rotation of the pedicle dart 335. A gentle forward motion is all that is necessary to provide this rotational locking.

Figure 40:
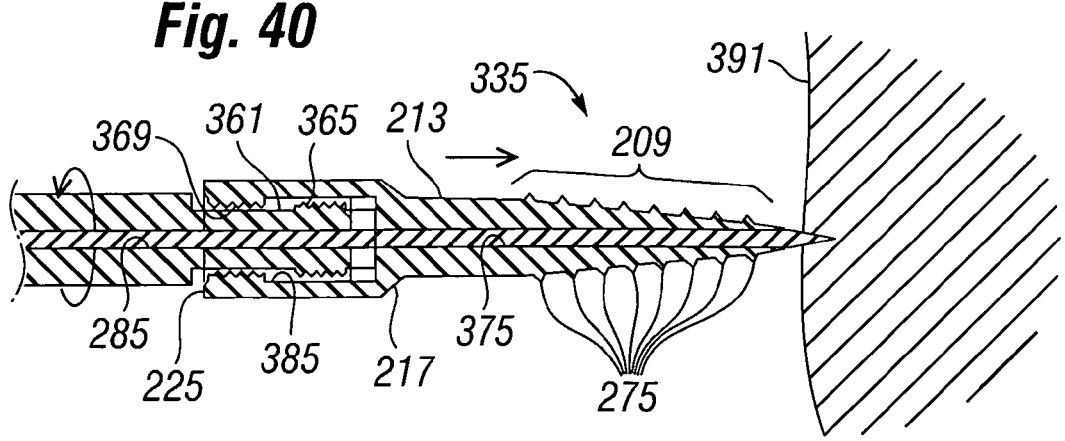
FIG. 40 illustrates the threads of the manipulator having just moved forward and into rotational locking engagement position with respect to the pedicle dart and shown adjacent a volume of bone into which the pedicle dart will be inserted.

Referring to FIG. 40, this locking relationship is seen. The pedicle dart now loaded onto the proximal end of the manipulator 373 so that it cannot be removed without a forward movement of the pedicle dart 335 with respect to the manipulator 373 followed by turning of the pedicle dart 335 with respect to the manipulator 373 to cause the internal threads 369 to engage and move through and then past the threaded section 363. As such the pedicle dart 335 is stably attached to the manipulator 373 without definite actions and manipulation by the practitioner.

Further, the guide pin 327 has been introduced into the main barrel bore 285 and pedicle dart guide pin through bore 375. Also, a mass of bone 391 is shown in schematic form. Typically the surgical practitioner will locate the point on the bone 391 where the pedicle dart 335 is to be inserted using the guide pin 327, tap the guide pin 327 until the proximal end 207 of the pedicle dart 335 begins to contact the bone 391. The guide pin is then removed either just before or just after the surgical practitioner begins turning the manipulator 373 with forward pressure.

Figure 41:
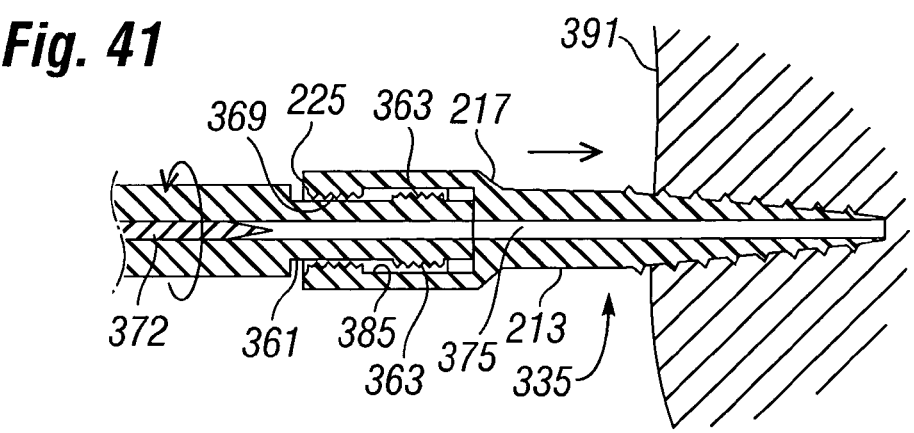
FIG. 41 illustrates the rotationally locked manipulator and pedicle dart of FIG. 39 shown bing further advanced into the volume of bone tissue along with withdrawal of the guide pin.

Referring to FIG. 41, a view illustrating withdrawal of the guide pin along with significant progress of the pedicle dart into the bone 391 is seen. Note that the manipulator 373 is still forward urged to cause the fingers 365 and 367 to remain immediately in front of the pair of depressions 381 and 383 and forwardly past the pair of walls 377 and 379 to maintain rotational lock of the manipulator 373 with respect to the pedicle dart 335.

Figure 42:
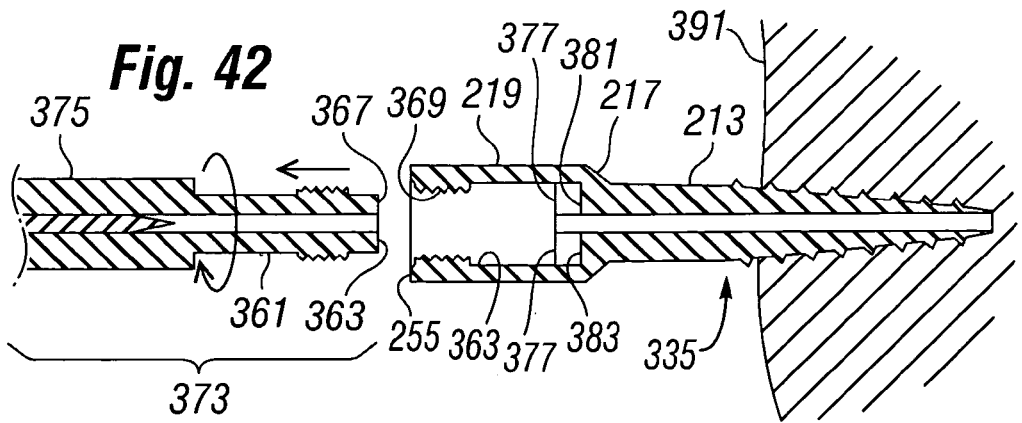
FIG. 42 illustrates final withdrawal of the manipulator from the pedicle dart after the threaded section moves out of threaded engagement with the internal threads of the pedicle dart and being moved away from the pedicle dart.

To leave the pedicle dart 335 located and embedded within the bone 391, the manipulator 373 is urged away from the pedicle dart so that the fingers 365 and 367 move rearwardly past the walls 377 and 379 to enable the main body 333 to freely rotate with respect to the pedicle dart 335. Counterclockwise rotation, preferred but not mandatory, continued with some continued rearward urging of the main body 333 will enable the rearward most thread of threaded section 363 into touching contact and engagement with the forward most thread of set of internal threads 369 at a point where the threaded section 363 moves out of threaded engagement with the internal threads 369 of the pedicle dart 335. This is best seen in FIG. 42. The pedicle dart 335 can be left in place, or used to make a starter bore into bone 391 so that a larger pedicle screw can be employed.

Figure 43:
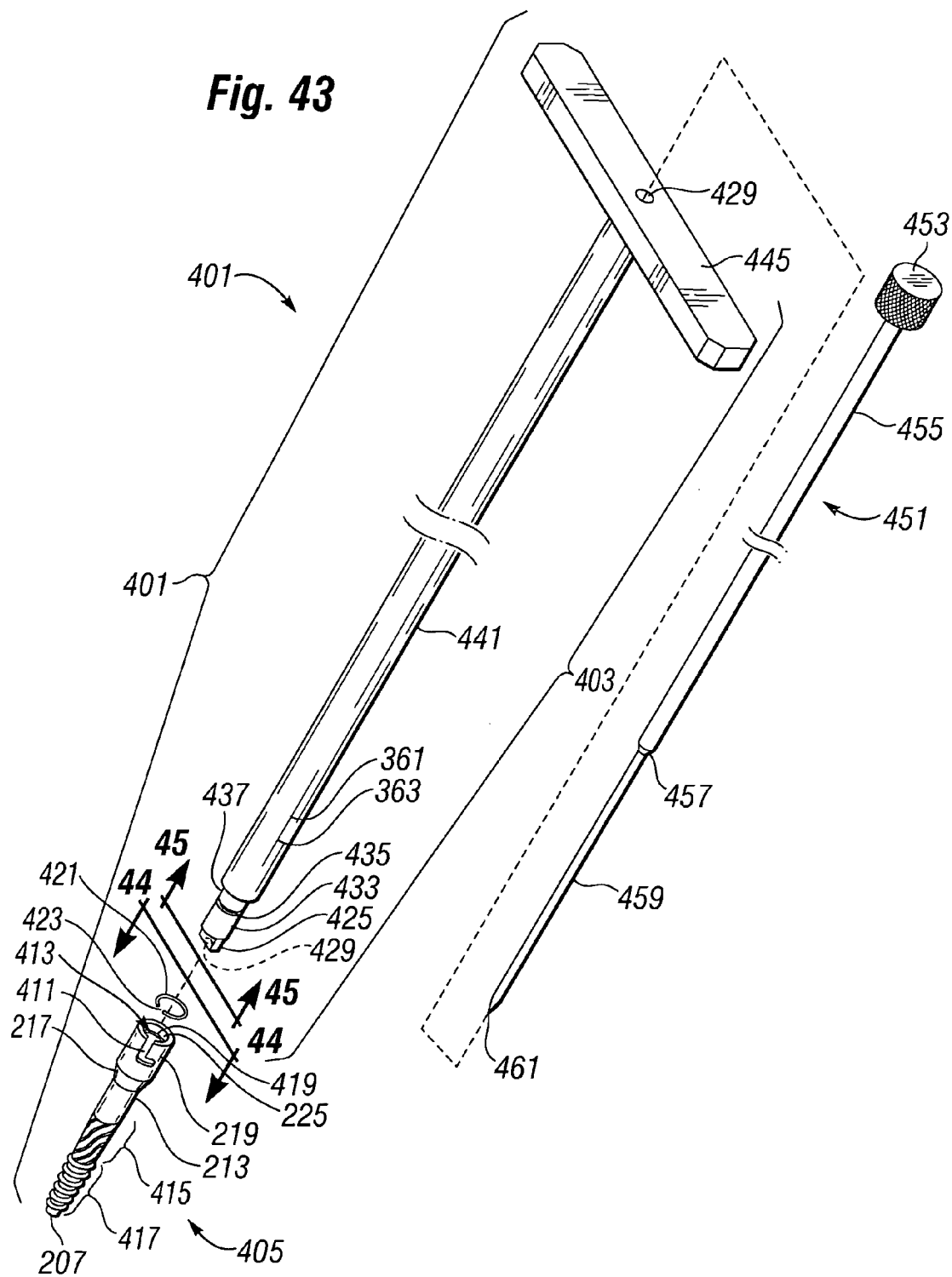
FIG. 43 is an exploded view of a further embodiment of the one step entry pedicular preparation device and system including a further embodiment of a manipulator which can manipulatably engage a pedicle dart 405 utilizing a straight axial force threshold for coupling and decoupling and which force of coupling and de-coupling can be controlled.

Referring to FIG. 43, a further embodiment of the one step entry pedicular preparation device and system is identified with the numeral 401 with uses guide pin 327, but a further embodiment of a manipulator 403 which can manipulatably engage a pedicle dart 405 utilizing a straight axial force threshold for coupling and decoupling.

Pedicle dart 405 has features which are similar to those seen with respect to pedicle dart 335, including proximal end 207, engagement sleeve 219, distal open end 225, frusto conical expansion section 217 and cylindrical section 213. New structures seen on the pedicle dart 405 include a hockey stick or "L" shaped slot 411 in order to provide the ability to retrieve a difficult or otherwise impeded pedicle dart such as pedicle dart 405. "L" shaped slot 411 extends partially along a bore 413. For Example, if the pedicle dart becomes wedged or jammed such that continued reverse rotation will not result in clearing the pedicle dart 405, the "L" shaped slot 411 can be used with a structure such as main body 333 having protruding key 247, such as manipulator 269. This need may be more pronounced in a manipulator 403 since it operates on a forward and reverse force threshold to engage and disengage.

Pedicle dart 405 may also have a differentiated thread set, including a coarse non cutting thread set 415, and a fine, self-tapping thread set 417. Also, a portion of a groove 419 seen just inside the distal open end 225. The groove 419 can support a spring tension open ring 421 seen exploded from the pedicle dart 405. Open ring 421 has a pair of ends 423. The open ring 421 has the ability for stable spring flexure and stable placement within the groove 419. In some cases, any groove or slot, such as "L" shaped slot 411 which crosses the path of the groove 419 can help in the placement, removal and testing of any open ring 421 provided.

To the right of open ring 421 is the most proximal end of the manipulator 403 which is seen as a laterally oblong block 425. At an end face 427 of the block 425, an opening of a main barrel bore 429 is seen. From the block 425, a transition to a proximal cylindrical section 433 is seen. Further distal to the proximal cylindrical engagement section 433, a force threshold locking groove 435 is seen. Further distal to the force threshold locking groove 435 is seen a the distal cylindrical engagement section 437. Further distal to the distal cylindrical engagement section 437 is a transition 439 to a main body 441 which happens to be shown as a constant exterior cross sectional cylindrical body.

A bar 445 is seen rigidly attached to the distal end of the main body 441. The main barrel bore 429 emerges at the distal end of the manipulator 403. A slightly different guide pin 451 includes a cylindrically shaped stop 453 attached to a shaft large diameter portion 455 which may have a diameter from about two to five millimeters in diameter. A transition 457 is seen between the shaft large diameter portion 455 and a shaft smaller diameter portion 459 having a diameter of about two millimeters in diameter. Where the guide pin 451 has a significant identifiable transition 457 with enough differential area to act as a stop, the cylindrically shaped stop 453 may not be necessary or it may have a different configuration. The significant identifiable transition 457 can range from a right angled radial surface to an angled transition to a tapering transition. The size of the cylindrically shaped stop 453 shown is built to both take significant impact and to provide a stop for the forward progress of the guide pin 451. At the proximal end of the smaller diameter portion 459 is a tip end 461. The use of different diameter in the guide pin 451 will enable a much more secure and supported connection of the cylindrically shaped stop 453 with respect to the shaft large diameter portion 455. Where the surgical practitioner strikes the cylindrically shaped stop 453, it should be able to transmit axial force through the guide pin 453 without bending of any of the structures seen in FIG. 43.

Figure 44:
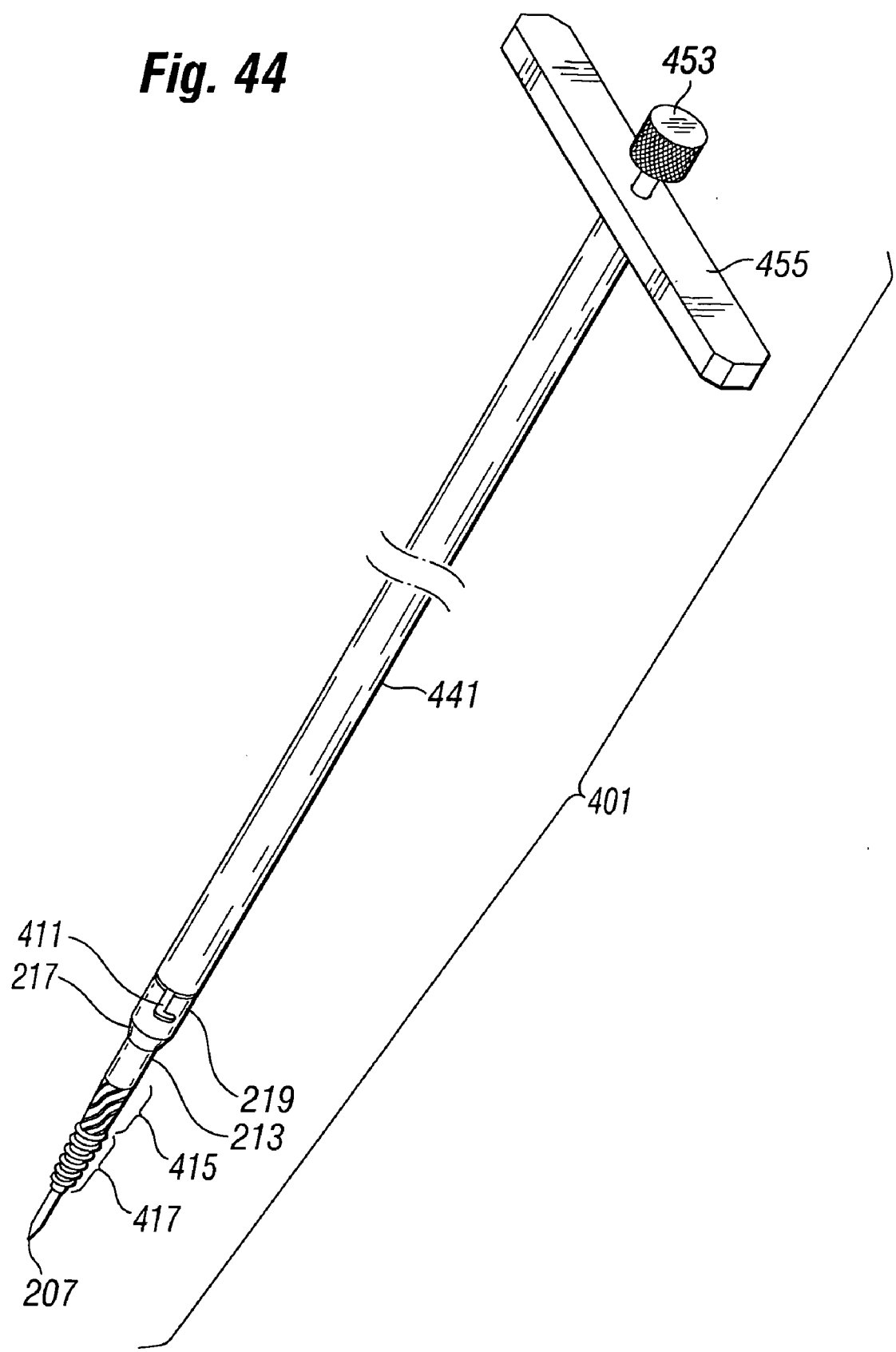
FIG. 44 is a perspective view of the embodiment of the one step entry pedicular preparation device and system seen in FIG. 43 but shown in assembled form.

Referring to FIG. 44, a perspective view of the embodiment of the one step entry pedicular preparation device and system 401 seen in FIG. 43 but is shown in assembled form.

Figure 45:
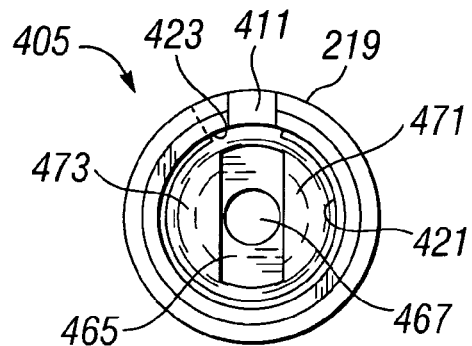
FIG. 45 is a view looking into the distal open end of the pedicle dart seen in FIGS. 43-45 and illustrating a rectangular depression used for rotational locking with respect to the manipulator.

Referring to FIG. 45, a view looking into the distal open end 225 of the pedicle dart 405 is seen. The "L" shaped slot 411 is seen, with the lateral terminal portion of the "L" shaped slot 411 seen as a slight dashed line to the left of the opening of the "L" shaped slot 411. Because the open ring 421 presents a smaller diameter than the inside of the distal open end 225, it appears slightly inwardly of and is therefore visible with respect to the inside of the distal open end 225. The groove 419 is such that the proximal cylindrical section 433 can be pushed past the open ring 421 without causing it to be dislodged from groove 419, and such that open ring 421 can expand to permit the proximal cylindrical section 433 to enter and slide past the open ring 421 at least until force threshold locking groove 435 reaches the inside of the open ring 421 to allow the open ring 421 to contract into the force threshold locking groove 435 to hold the pedicle dart 405 onto the proximal end of the manipulator 403.

Also seen in FIG. 45 is a rectangular depression 465 which is complementary to the laterally oblong block 425. Beyond the rectangular depression 465 a pedicle guide pin through bore 467 is seen. As a result, the guide pin 451 can be used independent of whether or not the pedicle dart 405 is attached to the manipulator 403. The surface between the open end of the rectangular depression 465 and the bore 413 further proximal with respect to the groove 419, may include a tapered shape as a pair of oppositely disposed angled surfaces 471 and 473 which can act to help orient the laterally oblong block 425 and rectangular depression 465 with respect to each other as they are brought in close proximity to each other. It is understood that "L" shaped slot 411 is not necessary for the spring tension open ring 421 to operate and "L" shaped slot 411 need not be present.

Referring to FIG. 45, a view looking into the end of the manipulator 403 is seen. The geometry of the protruding laterally oblong block 425 is seen to generally match the size and orientation of the rectangular depression 465. The spring tension open ring 421 is seen as having an inner diameter sufficient to springingly interfere with the proximal cylindrical section 433 to give a slight force resistance just before the proximal cylindrical section 433 can begin to slide past the spring tension open ring 421 to cause the force threshold locking groove 435 to be positioned so that the spring tension open ring 421 can springingly collapse within it to cause the pedicle dart 405 to be locked onto the manipulator 403. Some turning of the pedicle dart 405 with respect to the manipulator 403 may be necessary so that the protruding laterally oblong block 425 will seat in the rectangular depression 465 so that any turning force applied to the manipulator 403 will be transmitted directly to the pedicle dart 405.

Figure 46:
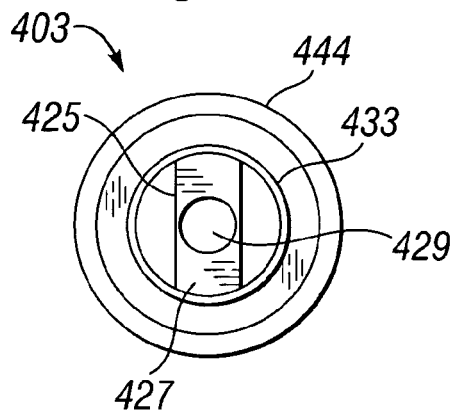
FIG. 46 illustrates a view looking into the end of the manipulator of FIGS. 43-44 and illustrating the oblong block which complementarily fits with the rectangular depression for rotational lock.
Figure 47:
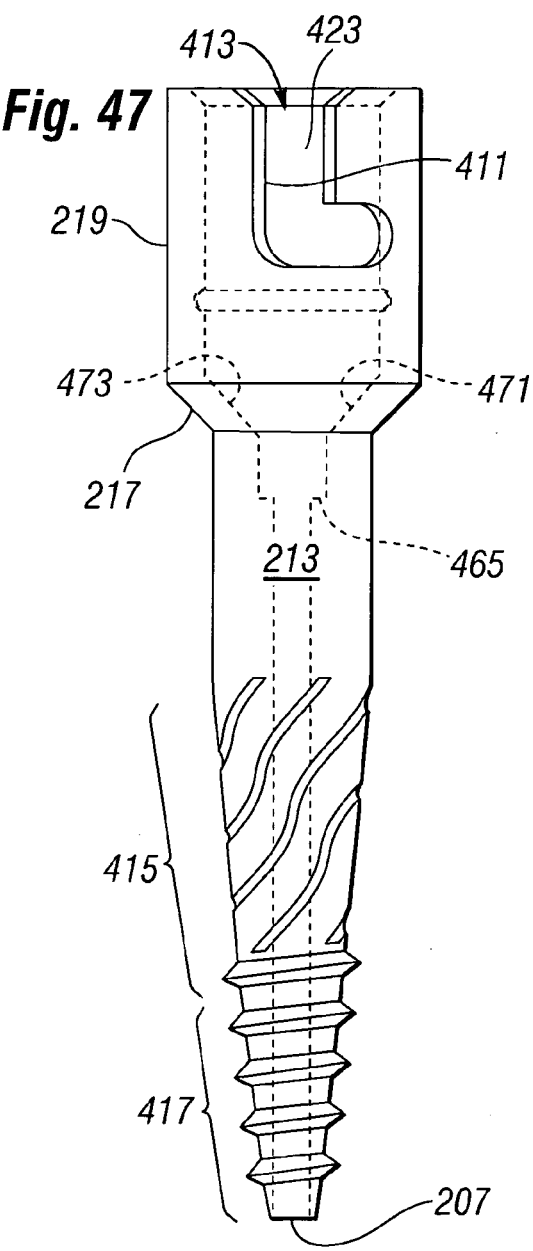
FIG. 47 illustrates a plan view of the pedicle dart further illustrating one configuration of the size and location of structures seen in FIGS. 43-46, including the lateral shape of the pair of oppositely disposed angled surfaces and the lateral shape of the rectangular depression used to provide rotational lock with respect to the manipulator.

Referring to FIG. 46, a plan view of the pedicle dart 405 illustrates the relative size and location of structures seen in FIGS. 43-45, including the lateral shape of the pair of oppositely disposed angled surfaces 471 and 473 as well as the shape of the rectangular depression 465.

Figure 48:
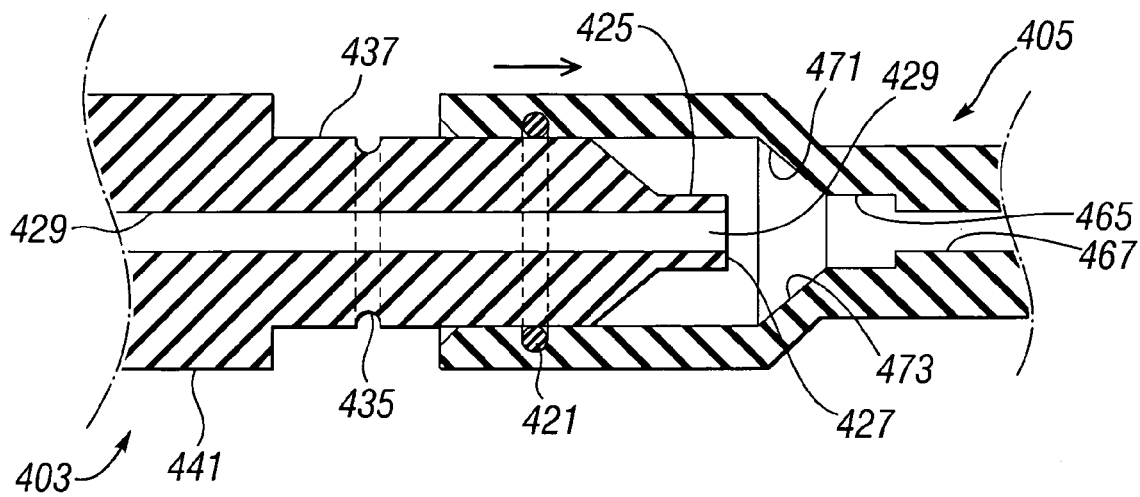
FIG. 48 illustrates an expanded sectional view which illustrates the manipulator having just pushed past and overcome the spring action of the spring tension open ring.

Referring to FIG. 48, an illustration of an expanded sectional view illustrates the proximal cylindrical section 433 of the manipulator 403 having just pushed past and overcome the spring action of the spring tension open ring 421 to attach the pedicle dart 405 to the manipulator 403.

Figure 49:
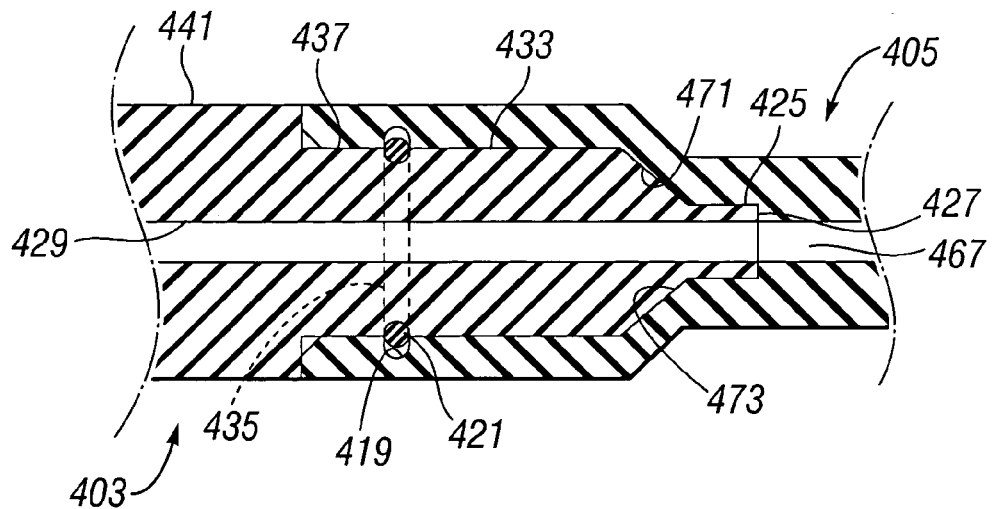
FIG. 49 is a view as seen in FIG. 48 in which the manipulator has continued pushing past the spring tension open ring until the force threshold locking groove is presented to the inside of the spring tension open ring allowing it to snap into the force threshold locking groove.

FIG. 49 is a view as seen in FIG. 48 in which the manipulator 403 has continued pushing past the spring tension open ring 421 until the force threshold locking groove 435 is presented to the inside of the spring tension open ring 421 allowing it to snap into the force threshold locking groove 435. Note that enough of the spring tension open ring 421 is seen remaining partially inside the groove 419 within the bore 413 of the pedicle dart 405 to provide a force lock preventing the pedicle dart 405 from becoming removed from the manipulator 403 so long as the force is less than that necessary to re-open the spring tension open ring 421. In this manner, the method of hold is an axial force method with a certain engagement force necessary to cause the proximal cylindrical section 433 to be able to move past the spring tension open ring 421, and a certain dis-engagement force necessary to cause the spring tension open ring 421 to fit back into the groove 419 within the bore 413 of the pedicle dart 405 to allow proximal cylindrical section 433 to be able to open spring tension open ring 421 so that the proximal cylindrical section 433 can back out of the bore 413 to disengage the pedicle dart 405 from the manipulator 403. These forces for both are affected by the strength of the spring tension open ring 421, but can be relatively shifted from forces of engagement and dis-engagement by tapering the forward edge of the proximal cylindrical section 433, and the forward edge of the force threshold locking groove 435.

Disc PediDart™

Figure 50:
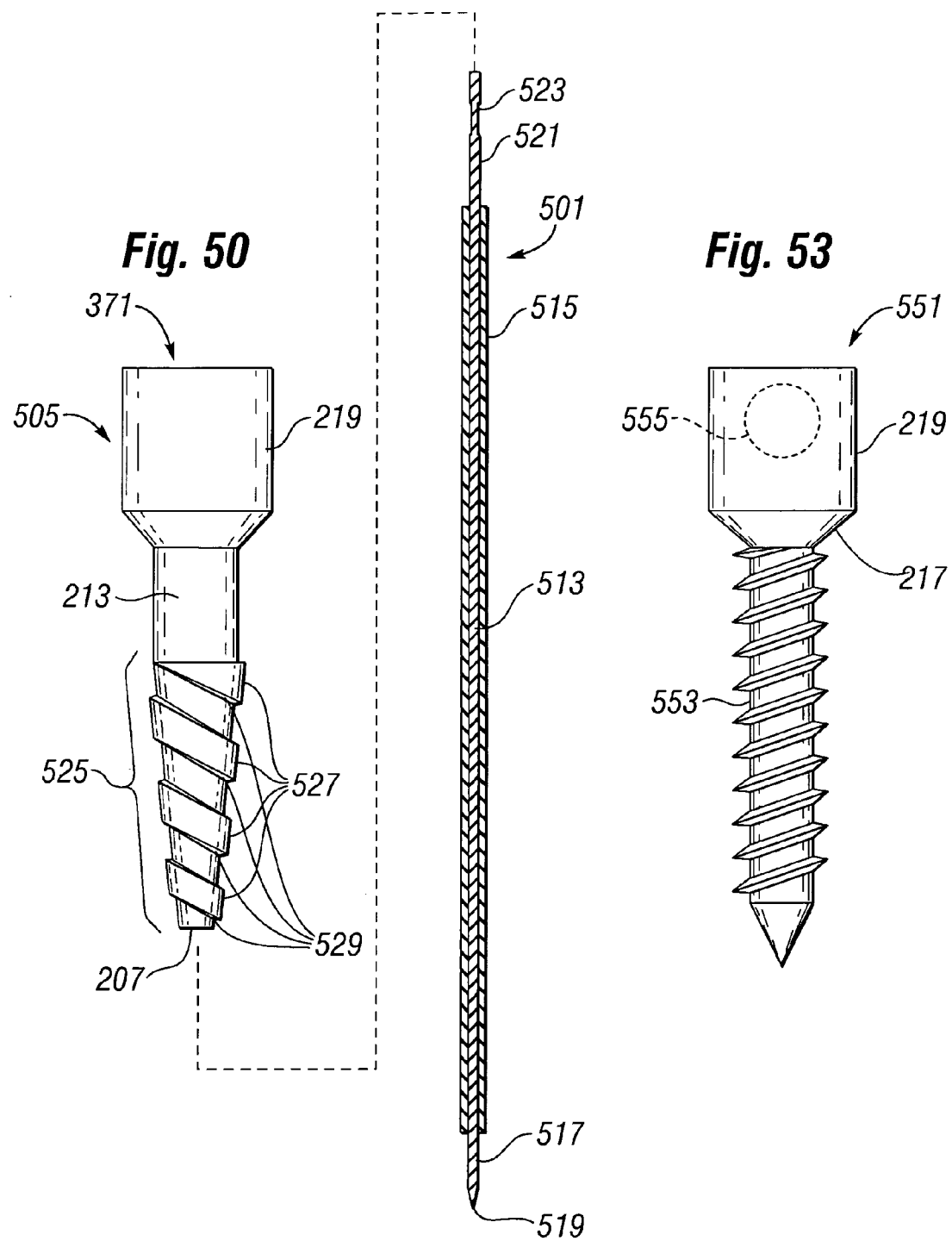
FIG. 50 is a side view of an insulated electromyography probe with a specialized flat threaded pedicle dart where the probe is sized to be overfit with the manipulator and specialized flat threaded pedicle dart to give access to the intervertebral space.

Referring to FIG. 50 a lateral view of a specialized insulated electromyography probe 501 sized to fit within the one step entry pedicular preparation device and systems 31, 201, 325, and 401, or a new specialized system is shown. Adjacent the insulated electromyography probe 501 a specialized flat threaded Disc PediDart™ pedicle dart 505 where the probe is sized to be overfit with the manipulator and specialized flat threaded pedicle dart to give access to the intervertebral space. The combination of the manipulators 269, 373 or 403 which work with the specialized insulated electromyography probe 501 and the flat threaded pedicle dart 505 may be referred to as a Disc PediDart™ intervertebral disc access system 511.

The insulated electromyography probe 501 has a main shaft 513 covered by an electrical insulating material 515 along its length except for a forward exposed length 517 and blunt or rounded point 519, and a rearward exposed length 521 and may include a nerve stimulation clip attachment area 523. Insulating material 515 can be of any type of electrically non-conductive material but it is preferable to have a material with a low modulus of friction on its exterior surface. The diameter of the electrical insulating material 515 which is expected to be the maximum diameter should be sufficient to fit through both the main barrel bore, such as main barrel bore 285 of any manipulator, such as manipulators 269, 373 or 403, as well as any guide pin through bore of any pedicle dart, such as pedicle darts 77, 95, 101, 105, 111, 205, 335, and 405, but especially pedicle dart 505.

Pedicle dart 505 has the same general structures already seen, such as cylindrical section 213, frusto conical expansion section 217 and engagement sleeve 219. From the cylindrical section 213, a tapering flat thread section 525 is seen having a wide flat thread 527 having a rounded, downwardly beveled forward surface 529 wrapped around the tapering flat thread section 525. Further, the leading edge is preferably curvingly beveled downward in order not to lacerate any nerves being pushed aside. The flat thread sections are for working in an environment which nerves may be present, so that any insertion of the pedicle dart 505 can, rather than threadably engage bone tissue, gently lift aside any layers to permit entry of the manipulators 269, 373 or 403. Attachment of the flat threaded pedicle dart 505 can be accomplished using any of the methods illustrated for pedicle darts 77, 95, 101, 105, 111, 205, 335, and 405 or other methods.

Figure 51:
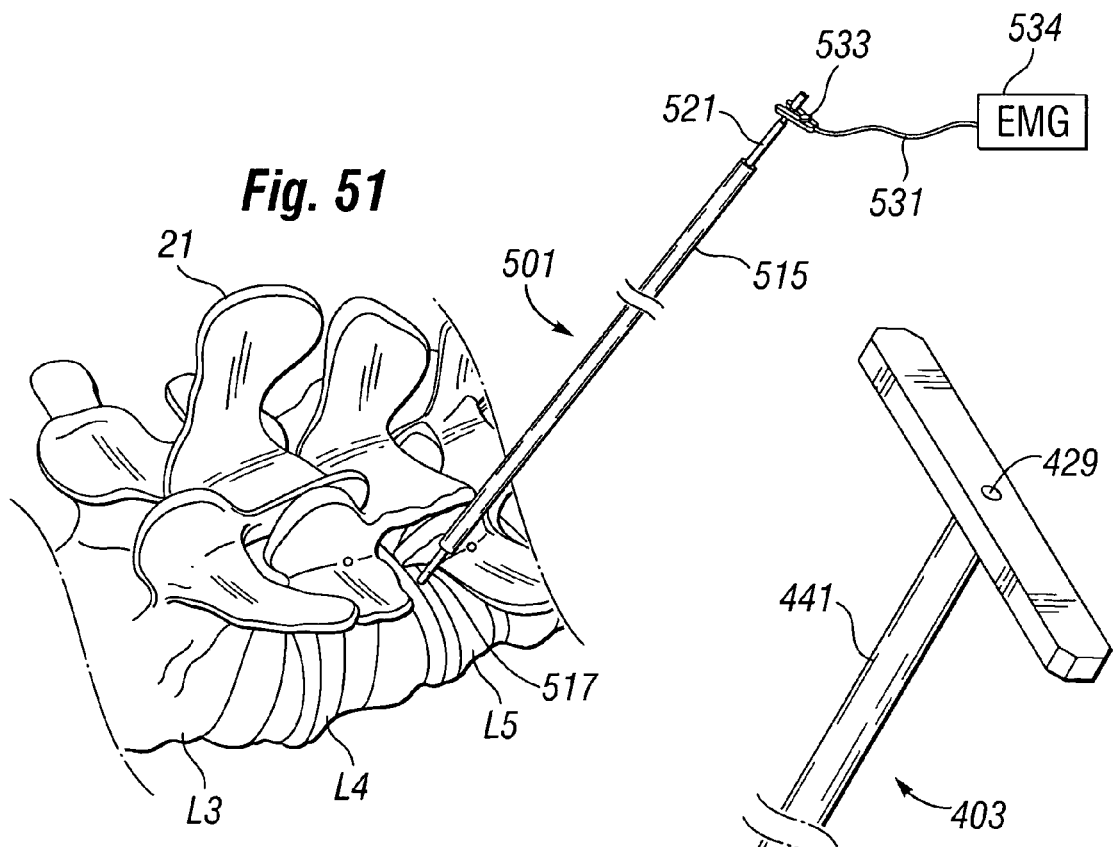
FIG. 51 is a perspective view of a few of the lower lumbar with an insulated electromyography probe being used to find a safe entry path into the intervertebral space and shown at a point where the insulated electromyography probe is just beginning to enter the intervertebral space and illustrating an electromyography instrument.

Referring to FIG. 51, a partial view of a few of the lower lumbar vertebrae L3, L4, L5 are shown. In the surgical procedure that follows, the insulated electromyography probe 501 will be used to find a safe entry path into the intervertebral space while the flat threaded pedicle dart 505 will be used to gently form an expanded stable path for any manipulator, such as manipulators 269, 373 or 403 while being guided along the outside diameter of the insulated electromyography probe and guide pin 501. After the flat threaded pedicle dart 505 reaches a sufficient level within the intervertebral space, insulated electromyography probe and guide pin 501 is removed while the combination of any one of the manipulators 269, 373 or 403 and the flat threaded pedicle dart 505 remains in place as a tiny access opening to the intervertebral space.

Referring to FIG. 51, the insulated electromyography probe and guide pin 501 is shown having an electrical attachment 531 via an electrical clip 533, to an electromyography instrument 535 shown as a box schematic bearing the letters "EMG" which can be any type of neuro-monitor. The electromyography instrument 535 enables a surgical practitioner to probe through the tissue while the forward exposed length 517 is able to signal to the electromyography instrument 535 if any nerves are contacted so that the surgical practitioner can avoid disrupting any nerves as the surgical practitioner probes a path to the intervertebral space. The view of FIG. 51 illustrates the insulated electromyography probe and guide pin 501 in a position after having just reached the intervertebral space.

Figure 52:
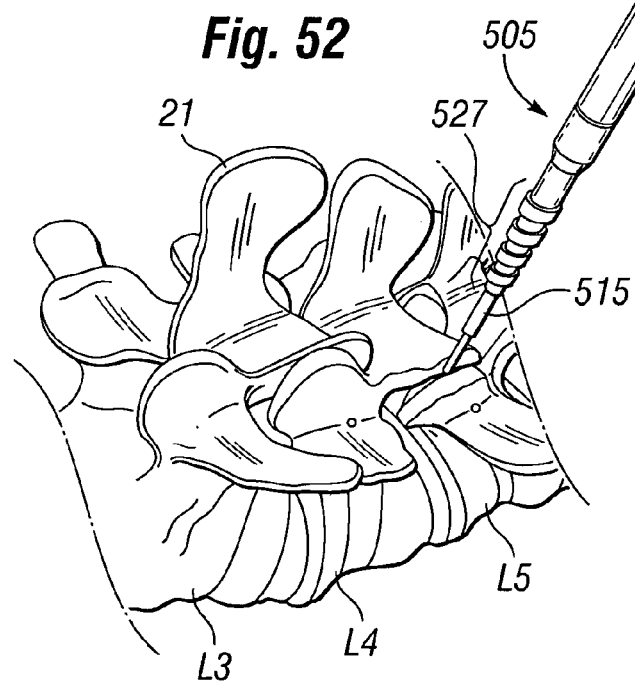
FIG. 52 is a perspective view similar to this seen for FIG. 51 but showing the electrical removal of the insulated electromyography probe from the electromyography instrument, and an advancement of the manipulator and flat threaded pedicle dart toward the intervertebral space and before arrival of the manipulator and flat threaded pedicle dart to a desired position in the intervertebral space when the electromyography probe can be rearwardly removed from the manipulator and flat threaded pedicle dart while the manipulator and flat threaded pedicle dart remains in place.

Referring to FIG. 52, the electrical clip 533 has been removed from the insulated electromyography probe and guide pin 501, and the intervertebral disc access system 511, including the manipulator 403 and flat threaded pedicle dart 505, is being moved gently toward the intervertebral space. Gentle turning of the intervertebral disc access system 511 will help gently displace any tissue evenly as the intervertebral disc access system 511 advances. Once the proximal end 207 of the flat threaded pedicle dart 505 reaches the intervertebral space, the insulated electromyography probe and guide pin 501 will be removed, leaving the intervertebral disc access system 511 in place with its bore leading from the main barrel bore 429 of the manipulator 403 through to the guide pin through bore 375 (not seen in FIG. 51). At this point in the procedure, other structures can be used to complete a biopsy, an injection or an electronic probing of the intervertebral space. A thin polymeric tube might be used for injection, and a cannula might be used for a biopsy.

One set of steps for an intervertebral disc access method using the Disc PediDart™ pedicle dart system of the embodiments herein might include:

(1) With the patient in a prone position on a radiolucent imaging table, position and align c-arm (for fluoroscopy) such that there is maximum width of the chosen disc and best definition of the superior and inferior end plates.

(2) The entry point of the guide pin should be at about two millimeters lateral to the border of the superior facet and in line with the central beam of the c-arm.

(3) Penetrate the skin with the blunt or rounded point 519 of the insulated electromyography probe and guide pin 501 and advance to the level of the transverse process.

(4) Begin nerve stimulation with electrical clip 533 of the electromyography instrument 535 attached to the electromyography probe and guide pin 501 or other neuro-monitor, at this level to avoid direct injury to the exiting nerve root. After safely bypassing the nerve root, enter the annulus of the disc.

(5) Remove the electrical clip 533 from the insulated electromyography probe and guide pin 501 and preferably position the blunt or rounded point 519 at the center of the disc if possible.

(6) Place the cannulated intervertebral disc access system 511 including the manipulator 403 and flat threaded pedicle dart 505 with the proximal end 207 of the flat threaded pedicle dart 505 over the rearward exposed length 521 of the insulated electromyography probe and guide pin 501 and over the electrical insulating material 515 and along the electrical insulating material 515, and advance through the small incision on the skin to contact the annulus. The adjacent exiting nerve root will be safely and gently pushed aside by the flat threaded pedicle dart 505.

(7) Impact the driver bar 445 to penetrate the annulus with the Disc PediDart™ cannulated intervertebral disc access system 511 including the manipulator 403 and flat threaded pedicle dart 505 and rotate the Disc PediDart™ cannulated intervertebral disc access system 511 including the manipulator 403 and flat threaded pedicle dart 505 to the proper level within the disc.

FIG. 53 is a plan view of a pedicle screw 551 which has an upper structure similar to that seen for pedicle darts in FIGS. 1-52, but which has a long even threaded profile seen as threaded shank 553 for implantation in the same manner as an ordinary pedicle screw 11 seen in FIG. 17. Pedicle screw 551 may have a tip 555, or it may have an optional guide pin through bore 467 where a combination of guide pin, such as guide pin 451, 327 or 35 can assist in implantation. Shown is an optional side area 557 which may be available for an interconnect member 23 as was seen in FIG. 17. As a result, it can be seen that the PediDart™ pedicle dart system of all the embodiments herein can be used for implantation of pedicle screws 551.

The shapes and sizes of all of the embodiments of the pedicle darts 77, 95, 101, 105, 111, 205, 335, 405 may vary. Dimensions which may be preferred in some instances include a tapered threaded section 209 which may have a length of about twenty five millimeters, but which may be divided into a five millimeter coarse non cutting thread set 415 and a twenty millimeter self-tapping thread set 417, a cylindrical section 213 which may have a length of about ten millimeters, and an engagement sleeve 219 length of about fifteen millimeters where these structures are present.

While the present system has been described in terms of a system which includes instrumentation, procedures and wide range of purposes to facilitate a difficult surgical task, one skilled in the art will realize that the structure and techniques of the present system can be applied to many instruments, including any instrument which has the ability to transmit high torque, selective attachment and detachment, and which accentuates the location and angle of approach of an entry into any point in the human body.

Although the system of the invention has been derived with reference to particular illustrative embodiments thereof, many changes and modifications of the systems shown may become apparent to those skilled in the art without departing from the spirit and scope of the inventive system. Therefore, included within the patent warranted hereon are all such changes and modifications as may reasonably and properly be included within the scope of this contribution to the art.

What is claimed:

1. A one step entry pedicular preparation device and system comprising:
   a guide pin having a first end having a sharp point and a second end opposite the first end;
   a manipulator having a main body having a first end and a second end, a rotation facilitation structure attached adjacent said second end of said main body, said main body having a main barrel bore extending through said main body from said second end of said main body to said first end of said main body;
   a pedicle dart having a first end having a narrowed tip and a second open end for user selectable rotatable fixed engagement by said first end of said main body, said pedicle dart having bone tissue engaging threads adjacent said first end of said pedicle dart and a pedicle dart guide pin through bore extending completely through said pedicle dart from said first end to said second open end and aligned with said main barrel bore of said main body of said manipulator, said pedicle dart guide pin through bore and said main barrel bore sized to admit said guide pin first end insertion through said barrel bore second end of said main body, through and beyond said first end of said pedicle dart when said pedicle dart is engaged with said manipulator;
   wherein the manipulator main body includes a protruding key nearer the first end of the main body than the second end of the main body, and wherein the pedicle dart includes a slot adjacent the second open end of the pedicle dart sized to interfit with the protruding key when the first end of said main body is inserted through the second open end of the pedicle dart to actuate said pedicle dart in at least one direction.

2. The one step entry pedicular preparation device and system as recited in claim 1 wherein said second end of said main body of said manipulator includes a block and wherein said pedicle dart includes a depression complementary to said block of said main body first end through said second open end of said pedicle dart for providing rotational fixation of said pedicle dart with respect to said manipulator when said block and said depression are interfittably engaged upon engagement of said pedicle dart with said manipulator.

3. The one step entry pedicular preparation device and system as recited in claim 1 wherein the manipulator includes a detent and the pedicle dart includes a raceway to receive the detent when the first end of the main body is inserted through the second open end of the pedicle dart.

4. The one step entry pedicular preparation device and system as recited in claim 1 wherein said bone tissue engaging threads have an axial length of about twenty five millimeters.

5. The one step entry pedicular preparation device and system as recited in claim 1 wherein said bone tissue engaging threads have a thread pitch of from about four to about six per centimeter of axial length.

6. The one step entry pedicular preparation device and system as recited in claim 1 wherein said narrowed tip at said first end of said pedicle dart has a diameter of about two millimeters.

7. The one step entry pedicular preparation device and system as recited in claim 1 wherein said bone tissue engaging threads are low height threads having a height of from about two tenths to about six tenths of a millimeter.

8. The one step entry pedicular preparation device and system as recited in claim 1 wherein said bone tissue engaging threads have a width of from about two tenths to about six tenths of a millimeter.

9. The one step entry pedicular preparation device and system as recited in claim 1 wherein said first end of said pedicle dart at said narrowed tip and surrounding said pedicle dart guide pin through bore has a thickness of from about one tenth of a millimeter to about five tenths of a millimeter.

10. The one step entry pedicular preparation device and system as recited in claim 1 wherein said guide pin has a diameter of about two millimeters.

11. The one step entry pedicular preparation device and system as recited in claim 1 wherein said rotation facilitation structure is a bar attached at a right angle adjacent said second end of said main body, and wherein said barrel bore extends through said bar.

12. The one step entry pedicular preparation device and system as recited in claim 1 wherein said rotation facilitation structure is a navigation structure carrying a plurality of structures which are spatially machine recognizable, and wherein said barrel bore extends through at least a portion of said navigation structure.

13. The one step entry pedicular preparation device and system as recited in claim 1, wherein the manipulator includes a bore that receives the detent and a spring to provide a biasing force on the ball.

14. A one step entry pedicular preparation device and system comprising:
   a guide pin having a guide pin body first end having a sharp point and a second end opposite the first end having a stop larger than said guide pin body;
   a pedicle dart having a first end having a narrowed tip and a second end, said pedicle dart having bone tissue engaging threads adjacent said first end of said pedicle dart and a pedicle dart guide pin through bore extending completely through said pedicle dart from said first end to said second end, the pedicle dart having a slot proximate the second end, the slot having a first portion and a second portion;
   a manipulator having a main body having a first end and a second end, a main bore extending through said manipulator from said second end of said manipulator to said first end of said manipulator, a protruding key extending form the main body, said first end of said manipulator attachable to said second end of said pedicle dart by at least one of force movement of said manipulator toward said pedicle dart so that the protruding key slides within the first portion of the slot, turnably urging said manipulator toward said pedicle dart and turning a threaded structure rotatable with respect to said manipulator, to engage said second end of said pedicle dart so that the protruding key slides within the second portion of the slot.

15. The one step entry pedicular preparation device and system as recited in claim 14 wherein at least one of said manipulator and said pedicle dart includes a projection and the other of said manipulator and said pedicle dart includes a complementary space for receiving said projection to rotatably lock pedicle dart rotationally with respect to said manipulator.

16. The one step entry pedicular preparation device and system as recited in claim 14, wherein the manipulator includes a detent and the pedicle dart includes a raceway to receive the detent when the first end of the manipulator is inserted into the second end of the pedicle dart.

17. A one step entry pedicular preparation device and system for implantation comprising:
   a guide pin having a first end having a sharp point and a second end opposite the first end;
   a manipulator having a main body having a first end and a second end, a rotation facilitation structure attached adjacent said second end of said main body, said main body having a main barrel bore extending through said main body from said second end of said main body to said first end of said main body;
   a pedicle dart having a first end having a narrowed tip and a second open end for user selectable rotatable fixed engagement by said first end of said main body, said pedicle dart having bone tissue engaging threads adjacent said first end of said pedicle dart and a pedicle dart guide pin through bore extending completely through said pedicle dart from said first end to said second open end and aligned with said main barrel bore of said main body of said manipulator, said pedicle dart guide pin through bore and said main barrel bore sized to admit said guide pin first end insertion through said main barrel bore second end of said main body, through and beyond said first end of said pedicle dart when said pedicle dart is selectably engaged with said manipulator;
   a pedicle screw for implantation utilizing said pedicle dart to assist in implantation, said pedicle screw having a first end having a narrowed tip and a second open end for user selectable rotatable fixed engagement by said first end of said main body, said pedicle screw having a predominantly constant cross section bone tissue implantation threads adjacent said first end of said pedicle screw and at least one of a pedicle screw guide pin through bore extending completely through said pedicle screw and a solid pointed tip at said first end;
   wherein the manipulator includes a movable detent and the pedicle dart includes a raceway to receive and engage the detent.

18. The one step entry pedicular preparation device and system as recited in claim 17, wherein the manipulator includes a protruding key and the pedicle dart includes a slot sized to interfit with the protruding key when the first end of the manipulator is inserted into the second end of the pedicle dart.

* * * * *